(12) United States Patent
Leblond et al.

(10) Patent No.: US 6,239,284 B1
(45) Date of Patent: May 29, 2001

(54) AROMATIC TETRACYCLIC COMPOUNDS OF THE RETINOID TYPE METHOD FOR PREPARING AND USE

(75) Inventors: Bertrand Leblond; Abdallah Deyine, both of Rouen; Alain-René Schoofs, Courbevoie; Pierre Germain, La Grande Motte; Bernard Pourrias, Bièvres, all of (FR)

(73) Assignee: Centre Europeen de Bioprospective-CEB (FR)

( * ) Notice: Subject to any disclaimer, the term of this patent is extended or adjusted under 35 U.S.C. 154(b) by 0 days.

(21) Appl. No.: 09/353,926

(22) Filed: Jul. 15, 1999

Related U.S. Application Data

(63) Continuation-in-part of application No. PCT/FR97/02223, filed on Dec. 5, 1997.

(51) Int. Cl.$^7$ ............... C07D 307/79; C07D 257/04; C07C 63/66; C07C 63/74; C07C 233/65; C07F 9/38
(52) U.S. Cl. ............... 548/253; 549/405; 562/8; 562/490; 562/491
(58) Field of Search ............... 548/253; 549/405; 562/490, 491

(56) References Cited

U.S. PATENT DOCUMENTS

| | | | |
|---|---|---|---|
| 5,455,265 | * 10/1995 | Chandraratna | 514/448 |
| 5,514,825 | 5/1996 | Vuligonda et al. | 558/426 |
| 5,523,457 | * 6/1996 | Starrett et al. | 560/24 |
| 5,675,024 | * 10/1997 | Teng et al. | 549/405 |
| 5,945,561 | * 8/1999 | Starrett et al. | 562/490 |
| 5,977,082 | * 6/1999 | Vuligonda et al. | 560/100 |

FOREIGN PATENT DOCUMENTS 93-21146 * 10/1993 (WO) ............... 562/490

OTHER PUBLICATIONS

M.I. Dawson, et al., "Effect of Structural Modifications in the C7–C11 Region of the Retinoid Skeleton on Biological Activity in a Series of Aromatic Retinoids," Journal of Medicinal Chemistry, vol. 32, No. 7, Jul. 1989, pp. 1504–1517, XP000563865.

Ling Jong, et al., "Conformational Effects on Retinoid Receptor Selectivity. I. Effect of 9–Double Bond Geometry on Retinoid X Receptor Activity," Journal of Medicinal Chemistry, vol. 36, No. 18, Sep. 1993, pp. 2605–2613, XP000563864.

M.F. Bochem. et al., "Synthesis and Structure—Activity Relationships of Novel Retinoid X Receptor–Selective Retinoids," Journal of Medicinal Chemistry, vol. 37, No. 18, Sep. 1994, pp. 2930–2941, XP000615432.

H. Kagechika, et al., "Retinobenzoic Acids. Structure–Activity Relationships of Aromatic Amides with Retinoidal Activity," Journal of Medicinal Chemistry, vol. 31, No. 11, Nov. 1988, pp. 2182–2192, XP000608417.

* cited by examiner

*Primary Examiner*—Floyd D. Higel
(74) *Attorney, Agent, or Firm*—Schnader Harrison Segal & Lewis LLP

(57) ABSTRACT

The invention concerns aromatic tetralcyclic compounds of the retinoid type of general formula (I). The invention also concerns the method for preparing them and the pharmaceutical compositions containing at least one of said compounds.

12 Claims, 3 Drawing Sheets

AROMATIC TETRACYCLIC COMPOUNDS OF THE RETINOID TYPE METHOD FOR PREPARING AND USE

Figure 1:
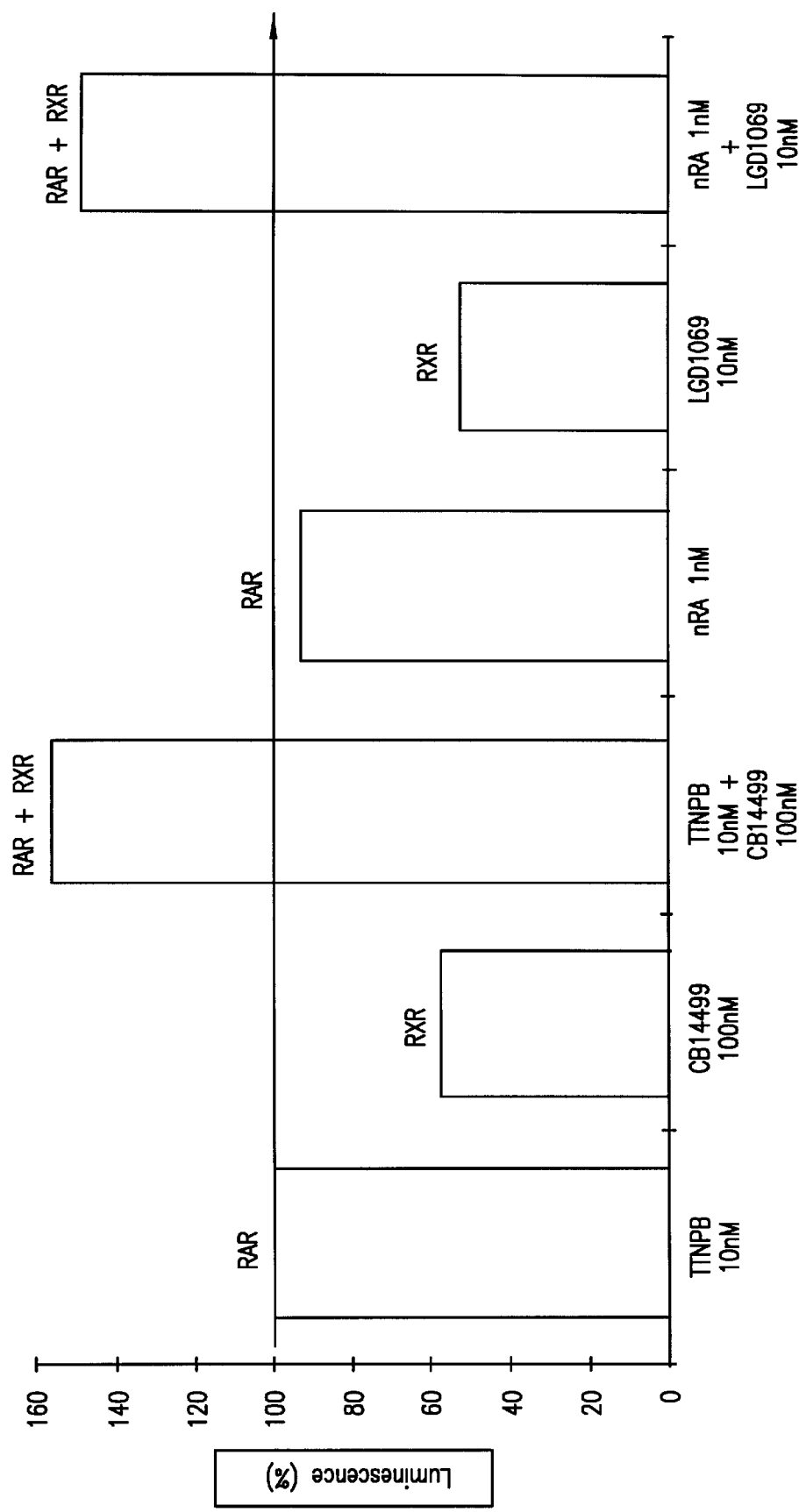

This application is a continuation-in-part of PCT/FR97/02223 filed Dec. 5, 1997.

This invention relates to tetracyclic aromatic compounds of the retinoid type of general formula:

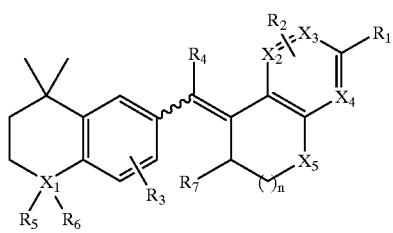

(I)

in which:
$R_1$ is chosen from among a hydrogen atom, a lower alkyl group, a group of formula —$PO_3H_2$, —$CH_2OH$, —OH, —CHO, —COOH, —$COR_8$, —$CH_2OCOR_9$, —SH, —S-alkyl, —$NH_2$, —$NHCOOR_{10}$, p-hydroxyphenylaminocarbonyl, tetrazol-5-yl-aminocarbonyl, tetrazol-5-yl, 5-trifluoromethyl-tetrazoyl, and when it is possible their salts with physiologically tolerated acids, where $R_{10}$ is a lower alkyl or aralkyl group and $R_8$ and $R_9$ are chosen from among:

a hydrogen atom, an —OH group, a lower alkyl group, or a group of formula —$OR_{11}$, where $R_{11}$ represents an alkyl group, which may be branched or not, having from 1 to 20 carbon atoms, an alkenyl group which may be branched or not, having from 2 to 20 carbon atoms, an aryl or aralkyl group, or an amine group of formula:

in which r and r', identical or different, represent a hydrogen atom, a lower alkyl group, an aryl or aralkyl group, an α-aminoacid group, a sugar group or a heterocyclic group in which r and r' taken together form a heterocyclic ring.

$R_2$ is chosen from among a hydrogen atom, a halogen atom and more particularly a fluorine atom, a lower alkyl group, a group of formula —COOH, $OR_{11}$, —$SR_{11}$, —$(CF_2)_nCF_3$ where n is a whole number between 0 and 10, or a $OCOR_{12}$ group, and when this is possible their salts with physiologically tolerated acids, or an amine group of formula:

in which r and r' have the same meaning as previously, and $R_{12}$ represents a hydrogen atom, a lower alkyl group, a fluoroalkyl group having 1 to 6 carbon atoms and from 3 to 7 fluorine atoms, an aryl group or an aralkyl group.

$R_3$ is chosen from among a hydrogen atom, a lower alkyl group, a halogen atom, a fluoroalkyl group having from 1 to 6 carbon atoms and from 3 to 7 fluorine atoms, or a group of formula —$OR_{13}$ where $R_{13}$ represents a hydrogen atom, a lower alkyl group, an aryl group, an aralkyl group, or a trifluoromethyl group.

$X_1$ is chosen from among an atom of carbon, an atom of oxygen or an atom of sulfur, and $R_5$ and $R_6$ are:
methyl or ethyl groups, in the case where $X_1$ is an atom of carbon,
nothing in the case where $X_1$ is an atom of oxygen or an atom of sulfur,
one or two atoms of oxygen in the case where $X_1$ is an atom of sulfur (the case of a sulphoxide —SO— or a sulphone —$SO_2$—).

$R_4$ is chosen from among a hydrogen atom, a halogen atom and more particularly a fluorine atom, a trifluoromethyl group, an aryl group, an aralkyl group, or a lower alkyl group, possibly substituted with a hydroxyl group, one or more atoms of fluorine, a lower alkoxy group or by a group with the formula —(C=O)$R_{14}$ in which $R_{14}$ represents a hydrogen atom, a lower group, a hydroxyl group, a lower alkoxy group or an amine group of formula:

in which r and r' have the same meaning as previously.

$X_2$ and $X_3$, identical or different, represent an atom of carbon, an atom of oxygen or an atom of nitrogen, or $X_2$-$X_3$ may be a single atom of sulfur, oxygen or nitrogen. Hence the nucleus carrying $X_2$ and $X_3$ can be a benzene, pyridine, thiophene, furane, or pyrrole nucleus.

$R_7$ is chosen from among a hydrogen atom, a trifluoromethyl group, a lower alkyl group, possibly substituted with one or more atoms of fluorine, or a —$OR_{15}$ where $R_{15}$ represents a hydrogen atom or a lower alkyl group.

$X_4$ represents a carbon atom or a nitrogen atom $X_5$ is chosen from among a carbon, oxygen, sulfur or nitrogen atom, a sulfide of formula —S—, a sulfoxide of formula —SO—, a sulfone of formula —$SO_2$—, an amine of formula —$NR_{16}$— where $R_{16}$ represents a hydrogen atom or a lower alkyl group, a group of formula —$COR_{17}$— or —$CO_2R_{17}$— where $R_{17}$ is a lower alkyl group or a benzyl group.

n is 0 or 1.

As examples of pharmaceutically acceptable salts of the previous compounds, one may mention, in a non-limitative way: the salts of acetic, hydrochloric, cinnamic, citric, formic, hydrobromic, hydriodic, hydrofluoric, malonic, methanesulfonic, oxalic, picric, maleic, lactic, nicotinic, phenylacetic, phosphoric, succinic, sulfuric and tartaric acids, ammonium salts, and salts of piperazine, diethylamine, nicotinamide, urea, sodium, potassium, calcium, magnesium, zinc, lithium, methylamine, dimethylamine, trimethylamine and tris(hydroxymethyl) aminomethane.

The term lower alkyl or alkoxy groups designates groups with 1 to 6 carbon atoms, straight chained or branched such as methyl, ethyl, propyl, isopropyl, butyl, isobutyl, secondary butyl, methoxy, ethoxy, propoxy, isopropoxy, butyloxy, isobutyloxy and secondary butyloxy groups.

Totally trans retinoic acid, a metabolite of vitamin A exhibits a large number of biological properties. Several molecules constructed from chemical modifications of this acid have been synthesized and have been shown to be biologically active. These synthetic analogues and their derivatives are called retinoids according to the definition of Sporn M. B. and Roberts A. B., *Ciba. Found Symp.*, 113, 1–5, 1985. Among these compounds, one may mention those described in European Patent Applications published under numbers 350 846, 303 186, 253 302, in the PCT International Patent Application published under the number WO 93/11755, or in U.S. Pat. Nos. 5,300,522, 5,420,273, 4,578,498 and the German Patents 3602473 and 3715955 as well as in the articles by Marcia I. Dawson et al. (J. Med. Chem., 1989, 32, 1504–1517; J. Med. Chem., 1993, 36, 2605–2613).

The compounds that show retinoid type activity are used in the treatment of mammals and more particularly man by chemoprevention and chemotherapy, notably in the treatment of numerous diseases such as dermatosis, acne, Darier's disease, psoriasis, icthyosis and eczema. These compounds are also used for the treatment and the prevention of cancerous diseases and numerous malignant hyperproliferative diseases such as cancers of the breast, the prostate, the lung, the head and the neck as well as certain types of cancer of epithelial origin and myelocytary leukaemias. The compounds that show retinoid type activity are also useful in the treatment and the prevention of arteriosclerosis, restenosis stemming from neo-intimal hyperproliferation, benign hyperproliferative pathologies such as endometrial hyperplasis, benign hypertrophy of the prostate, proliferative retinopathy, for the treatment of auto-immune diseases and immunological disorders such as erythematic lupus, for the treatment and the prevention of diseases associated with the metabolism of lipids and for the treatment of the effects of the sun on the skin.

However, these compounds of the retinoid type exhibit important secondary effects, notably a strong irritation of the skin and of the mucous membranes, interference with the lipid balance, and are even teratogens, which makes their clinical use a delicate matter (Kistler, A. et al. Arch Toxicol., 64: 616–622; "Retinoids in Oncology", edited by Waun Ki Hong & Reuben Lotan, The University of Texas M. D. Anderson Cancer Center, Houston, Tex., USA, Marcel Decker Inc., pages 127–146; "Retinoids in Clinical Practice", edited by Gideon Koren The Motherisk Program, The Hospital for Sick Children and The University of Toronto, Toronto, Ontario, Canada, Marcel Dekker Inc.).

The harmful effects reported above have led the applicant to look for aromatic polycyclic compounds of the retinoid type which are active notably in the treatment and prevention of the diseases mentioned previously but do not show any secondary effects.

The applicant has devised and then studied the properties of new compounds of the retinoid type corresponding to formula I, notably in comparison with the reference arotinoid (E)-4-[2-(5,6,7,8-tetrahydro-5,5,8,8-tetramethyl-naphthalenyl)-1-propenyl]benzoic acid (TTNPB).

The compounds of formula (I) of the invention include a double bond between the aromatic groups and can therefore exit in cis (Z) or trans (E) configurations or can be in the form of a mixture of cis/trans isomers.

So as to facilitate the understanding-of the isometry mentioned above, in the text that follows, FIG. (Ia) will be used to represent the trans configuration in which the aromatic groups are situated on either side of the double bond and FIG. (Ib) to represent the cis configuration in which the aromatic groups are situated on the same side of the double bond; it is understood that the invention refers to the mixture of the two isomers just as much as to each of the isomers taken separately.

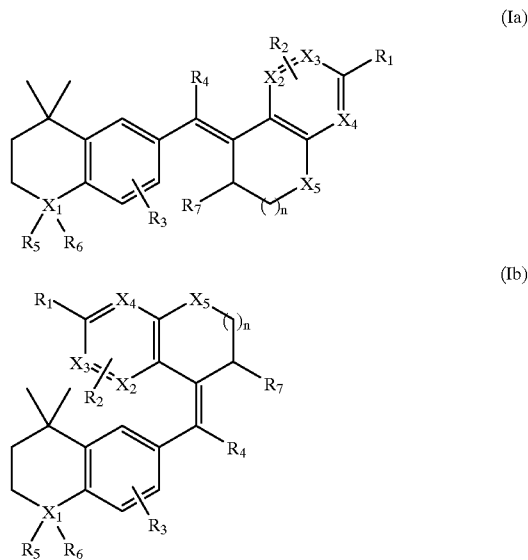

According to the nature of the groups $R_5$, $R_6$ and/or $R_7$, the compounds of formula (I) can contain one or more asymmetric carbons. The invention therefore relates as much to the racemic mixture as to each of the enantiomers.

The prior art and notably the patents and patent applications mentioned above, indicate logically the existence of cis and trans isomers but are concerned specifically with compounds of a trans configuration since this configuration is the one met with in the reference arotinoid mentioned above.

The research work carried out by the applicant on the compounds of general Formula (I) have led her to demonstrate that these compounds show an intrinsic activity that allows them to modulate proliferation and cellular differentiation, and that this permits their application in the treatment and the chemoprevention of diseases such as breast cancer, prostate cancer, lung cancer, cutaneous cancers and promyelocytary leukaemias in non-teratogenic compositions, and in the treatment of symptoms of diseases such as acne, Darier's disease, psoriasis, icthyosis and eczema.

Hence, the subjects of this invention are the aromatic polycyclic aromatic compounds of general Formula (I), previously defined, their method of preparation as well as their use in human and veterinary medicine, in dermatology and in cosmetics.

Among the compounds of Formula (I), a preferred series is that in which $R_2$ represents a hydrogen atom and $R_1$ is chosen from among a tetrazoyl group, a —COOH group, a —PO$_3$H$_2$ group and a —CONH$_2$ group.

The invention considers, by way of specific examples, the following compounds of Formula (I):

The acid (E) 3-[2-(5,6,7,8-tetrahydro-5,5,8,8-tetramethyl) naphthalenylmethylene]-dihydro-benzo[b]furane-5-carboxylic acid, designated CB93128 and corresponding to the following formula:

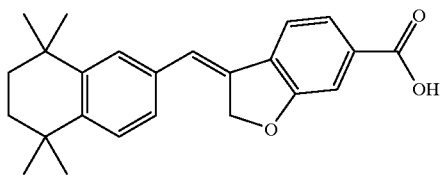

The acid (Z) 1-[2-(5,6,7,8-tetrahydro-5,5,8,8-tetramethyl) naphthalenylmethylene]-1,2,3,4-tetrahydronaphthalene-6-carboxylic acid, designated CB80830 and corresponding to the following formula:

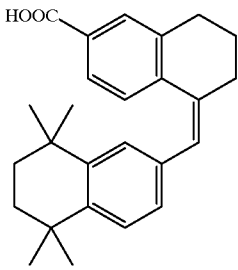

The acid (E) 1-[2-(5,6,7,8-tetrahydro-5,5,8,8-tetramethyl) naphthalenylmethylene]-1,2,3,4-tetrahydronaphthalene-6-carboxylic acid, designated CB66049 and corresponding to the following formula:

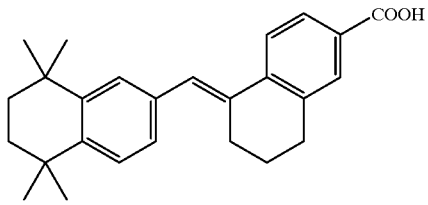

The acid (E) 5-[1-[2-(5,6,7,8-tetrahydro-5,5,8,8-tetramethyl)-2-naphthalenylmethylene]-1,2,3,4-tetrahydronaphthalenyl]-1H-tetrazole, designated CB44858 and corresponding to the following formula:

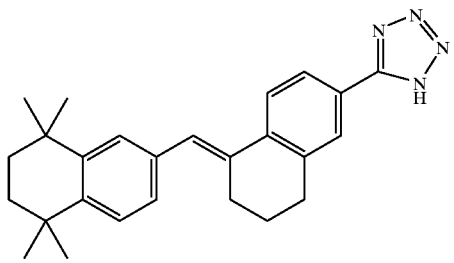

The acid (Z) 1-[2-(5,6,7,8-tetrahydro-3,5,5,8,8-pentamethyl)naphthalenylmethylene]-1,2,3,4-tetrahydronaphthalene-6-carboxylic acid, designated CB53261 and corresponding to the following formula:

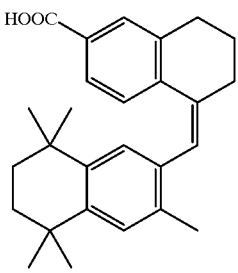

The acid (E) 1-[2-(5,6,7,8-tetrahydro-3,5,5,8,8-pentamethyl)naphthenylmethylene]-1,2,3,4-tetrahydronaphthalene-6-carboxylic acid, designated CB95970 and corresponding to the following formula:

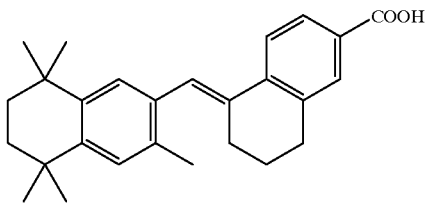

The compound (Z) 5-[1-[2-(5,6,7,8-tetrahydro-3,5,5,8,8-pentamethyl)naphthalenylmethylene]-1,2,3,4-tetrahydronaphthalenyl]-1H-tetrazole designated CB02305 and corresponding to the following formula:

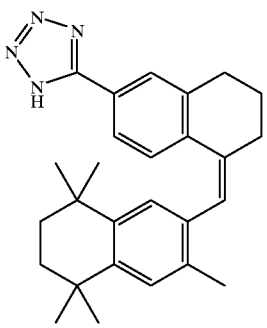

The compound (E) 5-[1-[2-(5,6,7,8-tetrahydro-3,5,5,8,8-pentamethyl)naphthalenylmethylene]-1,2,3,4-tetrahydronaphthalenyl]-1H-tetrazole designated CB58248 and corresponding to the following formula:

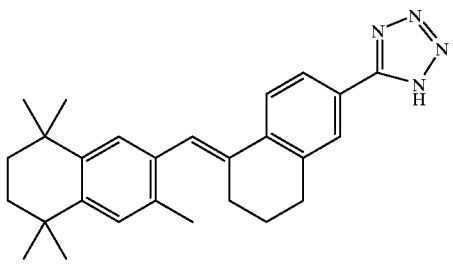

The acid (E) 1-[2-(5,6,7,8-tetrahydro-5,5,8,8-tetramethyl) naphthalenylmethylene]-2,3-dihydro-1H-indene-5-carboxylic acid; designated CB78937 and corresponding to the following formula:

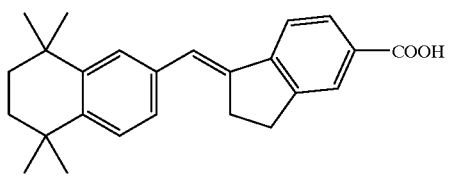

The acid (E) 5-[1-[2-(5,6,7,8-tetrahydro-5,5,8,8-tetramethyl)naphthalenylmethylene]-2,3,-dihydro-1H-indenyl]-1H-tetrazole, designated CB99811 and corresponding to the following formula:

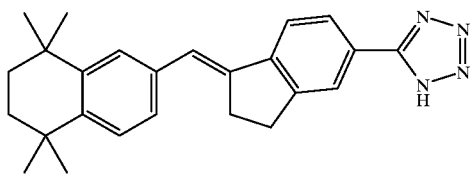

The acid (Z) 1-[2-[1-(5,6,7,8-tetrahydro-5,5,8,8-tetramethyl)naphthalenylmethylene]-2,3-dihydro-1H-indene-5-carboxylic acid designated CB27871 and corresponding to the following formula:

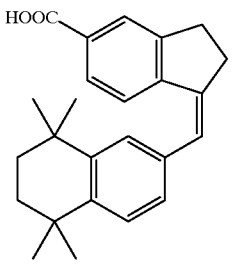

The compound (Z) 5-[1-[2-(5,6,7,8-tetrahydro-5,5,8,8-tetramethyl)naphthalenylmethylene]-2,3-dihydro-1H-indenyl]-1H-tetrazole, designated CB94083 and corresponding to the following formula:

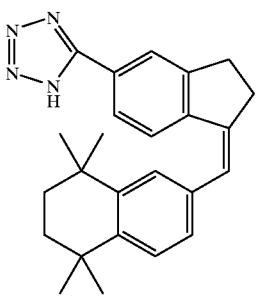

The acid (Z) 1-[2-(5,6,7,8-tetrahydro-3,5,5,8,8-pentamethyl)naphthalenylmethylene]-2,3-dihydro-1H-indene-5-carboxylic acid designated CB75403 and corresponding to the following formula:

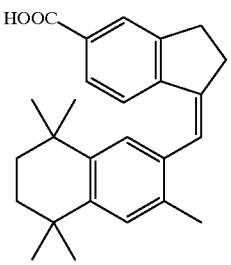

The compound (Z) 5-[1-[2-(5,6,7,8-tetrahydro-3,5,5,8,8-pentamethyl)naphthalenylmethylene]-2,3-dihydro-1H-indenyl]-1H-tetrazole designated CB02981 and corresponding to the following formula:

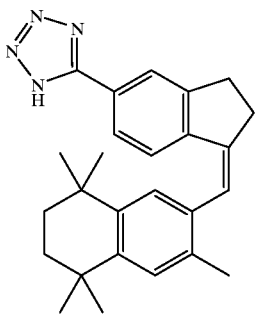

The acid (E) 1-[2-(5,6,7,8-tetrahydro-3,5,5,8,8-pentamethyl)naphthalenylmethylene]-2,3-dihydro-1H-indene-5-carboxylic acid designated CB40341 and corresponding to the following formula:

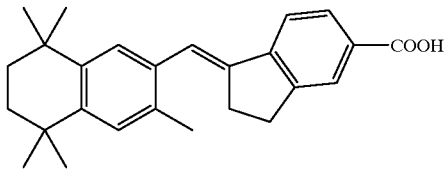

The compound (E) 5-[1-[2-(5,6,7,8-tetrahydro-3,5,5,8,8-pentamethyl)naphthalenylmethylene]-2,3-dihydro-1H-indenyl]-1H-tetrazole designated CB23804 and corresponding to the following formula:

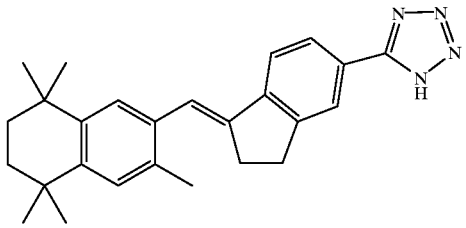

The acid (E) 1-[2-(5,6,7,8-tetrahydro-3,5,5,8,8-pentamethyl)naphthalenylmethylene]-2,3-dihydro-1H-indenyl-5-phosphonic acid designated CB69179 and corresponding to the following formula:

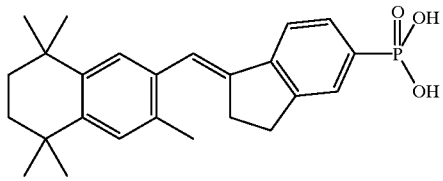

The acid (E) 1-[2-(5,6,7,8-tetrahydro-5,5,8,8-tetramethyl) naphthalenylmethylene]-2,3-dihydro-2-methyl-1H-indene-5-carboxylic acid designated CB52809 and corresponding to the following formula:

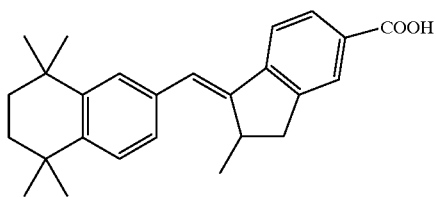

The compound (Z) 1-[2-(5,6,7,8-tetrahydro-5,5,8,8-tetramethyl)naphthalenylmethylene]-2,3-dihydro-2-methyl-1H-indene-5-amide designated CB96711 and corresponding to the following formula:

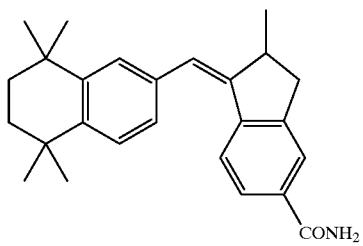

The acid (Z) 1-[2-(5,6,7,8-tetrahydro-5,5,8,8-tetramethyl) naphthalenylmethylene]-2,3-dihydro-2-methyl-1H-indene-5-carboxylic acid designated CB91261 and corresponding to the following formula:

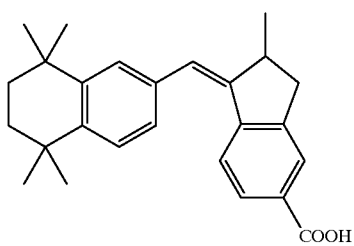

The compound (E) 5-[1-[2-(5,6,7,8-tetramethyl)naphthalenylmethylene]-2,3-dihydro-2-methyl-1H-indenyl]-1H-tetrazole designated CB69831 and corresponding to the following formula:

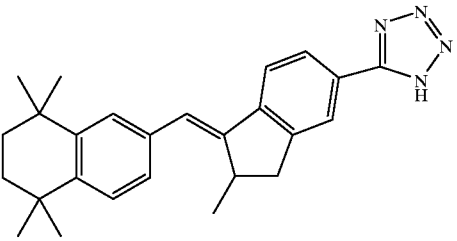

The invention also relates to the preparation of the compounds of formula (I) and the pharmaceutical or cosmetic compositions that contain at least one of said compounds as an active ingredient.

The compounds of the invention can be prepared by a Wittig reaction between a phosphonium salt and a ketone according to the following diagram:

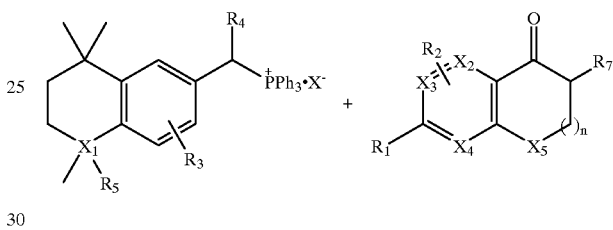

They can also be prepared by a Wittig reaction consisting of condensing a carbonyl compound (aldehyde or ketone) with a phosphonium salt according to the following diagram:

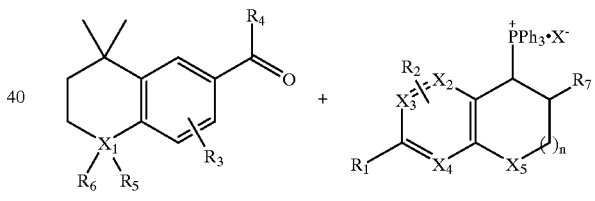

The compounds of the invention can also be prepared by a Horner-Emmons reaction consisting of condensing a carbonyl compound (aldehyde or ketone) with a phosphonate in accordance with the same principle as the diagrams above with a phosphonate replacing a phosphonium salt. They can also be obtained by dehydration of tertiary alcohols corresponding to one of the following formulae:

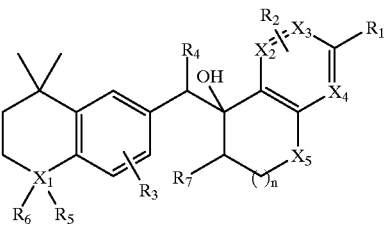

-continued

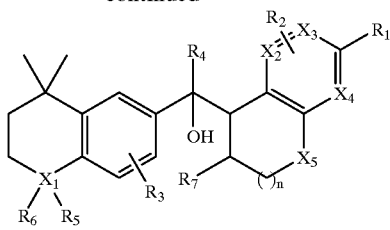

The compounds of the invention can also be prepared by a Suzuki type coupling reaction (A. R. de Lera et al., Synthesis, 285, 1995) according to the following diagram.

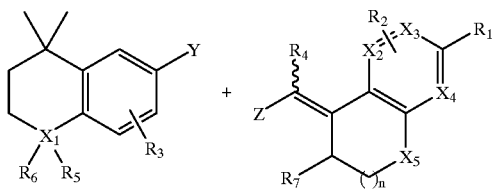

In the formulae above, Y=B(OH)$_2$ and Z=OTf, I, Br; or Y=OTf, I, Br and Z=B(OH)$_2$ and $X_1$, $X_2$, $X_3$, $X_4$, $X_5$, $R_1$, $R_2$, $R_3$, $R_4$, $R_5$, $R_6$ and $R_7$ have the same meanings as in formula (I).

The methods above are given as non-limitative examples and any other method that allows one to create double bonds or carbon-carbon bonds can be used to prepare the compounds of the invention.

The cis and trans isomeric forms of the derivatives obtained by these various methods can be separated and purified either during the synthesis process by a change of solvent or addition of salt (March, J., Modern Organic Synthesis, 3rd Edition, Wiley Interscience, p. 845–854), or in the final stage, according to known techniques, such as, for example, recrystallisation, preparative HPLC or chromatography.

In addition, it is possible, from the derivatives of Formula (I) and from their cis and trans isomers obtained according to the preceding methods, to prepare other derivatives by usual reactions involving one or more of the groups $X_1$, $X_2$, $X_3$, $X_4$, $X_5$, $R_1$, $R_2$, $R_3$, $R_4$, $R_5$, $R_6$ and $R_7$. For example, one may mention the following reactions.

An ester of a carboxylic acid of Formula (I) in which $R_1$ is a —COOR$_{11}$ group can be saponified by known methods, for example, by treatment with alkaline solutions, more particularly by treatment with a hydro-alcoholic solution of sodium or potassium hydroxide at temperatures between ambient and the boiling point of the reaction mixture. The carboxylic acid thereby obtained can be converted into an amide via passage through an acid halide or converted into an amide directly-by using a peptide coupling reaction, for example, by using as a coupling agent carbonyl di-imidazole (CDI) and as amine the 5-aminotetrazole in solution in THF at ambient temperature (Paul R., Anderson G. W., J. Am. Chem. Soc., 82, 4596, 1960).

A carboxylic acid of Formula (I) in which $R_1$ is a —COOH group, can be converted by a known method, for example by treatment with thionyl chloride, in toluene or pyridine, or by phosphorus trichloride or phosphorus pentachloride in toluene, into an acid chloride. This acid chloride can be converted, into an ester by reaction with an alcohol, or into a corresponding amide by reaction with an amine.

A carboxylic acid or a carboxylic acid ester of Formula (I) in which $R_1$ is a —COOH or —COOR$_{11}$ group, can be reduced by known methods in such a way as to give the corresponding alcohol where $R_1$ is a —CH$_2$OH group.

A sulfide of Formula (I), in which $X_1$ is an atom of sulfur (—S—), can be oxidized to a sulfoxide (—SO—) or a sulfone (—SO$_2$—), $R_6$ and $R_7$ are then identical or different and represent either nothing (the case of a sulfide: —S—), or an oxygen (the case of a sulfoxide: —SO—) or two oxygens (the case of a sulfone —SO$_2$—). The oxidation of a sulfide group can be carried out by using oxidizing agents such as periodates (for example sodium periodate) or by using organic peracids such as m-chloroperbenzoic acid (mCPBA). When the oxidation is carried out by using an organic peracid, about 1 equivalent allows one to obtain a tulfoxide while the use of 2 equivalents of peracid leads to the sulfone.

An amide of Formula (I) in which $R_1$ is a —CONrr', can be reduced by known methods in a way that gives an aldehyde ($R_1$=—CHO), for example by di-isobutyl aluminum hydride in solution in toluene, preferably by using THF as reaction solvent at temperature's between −78° C. and ambient.

An aldehyde of Formula (I) in which $R_1$ is a —CHO group, can be oxidized by known methods in a way that gives a carboxylic acid ($R_1$=—COOH) or a carboxylic acid ester ($R_1$=—COOR$_{11}$), for example by the Corey method (Corey E. J. et al., J. Am. Chem. Soc., 90, 5616, 1968) making use of manganese dioxide, sodium cyanide, acetic acid and methanol at ambient temperature.

A nitrile derivative of Formula (I) in which $R_1$ is a —CN group, can be hydrolyzed to the corresponding carboxylic acid ($R_1$=—COOH) by known methods, for example, by treatment with alkaline bases, more especially by treatment with a hydro-alcoholic solution of sodium or potassium hydroxide at temperatures between ambient and the boiling point of the reaction mixture.

A nitrile derivative of Formula (I) in which $R_1$ is a —CN group, can be converted into a 1H-tetrazole by known methods, for example by treatment with trimethylsilane azide N$_3$SiMe$_3$, in the presence or not of a catalyst such as dibutyl tin oxide (Bu)$_2$SnO in aromatic solvents preferably toluene or benzene at temperatures between ambient and the boiling point of the reaction mixture.

A brominated, iodated or chlorinated aromatic derivative of Formula (I) in which $R_1$ is an atom of bromine, iodine or chlorine, can be converted by known methods into a nitrile derivative ($R_1$=—CN), for example by the Rosenmund-von Braun reaction using cuprous cyanide in a solvent, preferably dimethyl formamide or quinoline at temperatures between ambient and the boiling point of the reaction mixture.

A brominated, iodated or chlorinated aromatic derivative of Formula (I) in which $R_1$ is an atom of bromine, iodine or chlorine, can be converted by known methods. into a carboxylic acid ($R_1$=—COOH), for example by halogen-metal exchange using butyl lithium (primary, secondary or tertiary) in solution in THF in the cold (−78° C. to 0° C.) and condensation of carbon dioxide then being raised again to ambient temperature.

A brominated, iodated or chlorinated aromatic derivative of Formula (I) in which $R_1$ is an atom of bromine, iodine or chlorine, can be converted by known methods into a carboxylic acid ester ($R_1$=—COOR$_{11}$), for example by halogen-metal exchange using butyl lithium (primary, secondary or tertiary) in solution in THF in the cold (−78° C. to 0° C.) and condensation onto an alkyl chloroformate.

The derivatives of Formula (I) in which $R_1$ is a —COOH or -tetrazoyl group, can be converted by known methods into salts by. physiologically acceptable, non-toxic, inorganic or organic bases, for example into alkali metal salts or into alkaline earth metal salts, for example sodium, potassium, magnesium or calcium salts as well as ammonium salts or non-toxic amine salts.

A carboxylic acid of Formula (I) in which $R_1$ is a —COOH group can be converted by a known method, for example, by a Curtius type rearrangement, with diphenyl phosphorane azide in the presence of triethylamine in toluene at 80° C., followed by an addition of an alcohol of the $R_{10}OH$ type, preferably methyl alcohol ($R_{10}$=Me) or benzyl alcohol ($R_{10}$=benzyl), into a carbamate —NHCOOR$_{10}$, which by treatment with 10% aqueous caustic soda ($R_{10}$=Me) or by hydrogenation ($R_{10}$=benzyl) leads to an aniline of Formula (I) where $R_1$ is a —NH$_2$ group.

An aniline of Formula (I) where $R_1$ is a —NH$_2$ group can be converted by known methods of trifluoroacetylation, for example by using 2-(trifluoroacetyloxy)pyridine (TFAP) in ether at temperatures between 0° C. and the boiling point of the reaction mixture (T. Keumi et al., Bull. Chem. Soc. Jpn., 63, 2252, 1990), into the trifluoromethylated amide of Formula (I) where $R_1$ is a —NH(C=O)CF$_3$ group. The trifluoromethylated amide of Formula (I) can be converted by known methods into a chlorinated imine, preferably by using triphenylphosphine and carbon tetrachloride (K. Tamura et al., J. Org. Chem., 58, 32, 1993), to lead to the compound of Formula (I) where $R_1$ is a —N=C(CF$_3$) (Cl) group.

A trifluoroacetimidoyl chloride of Formula (I) where $R_1$ is a —N=C(CF$_3$) (Cl) group can be cyclized by known methods, preferably by sodium azide in acetic acid at 70° C. (D. Armour et al., Bioorg. & Med. Chem. Lett., 6, 1015, 1996) to lead to a tetrazole of formula (I) where $R_1$ is a group with the following formula:

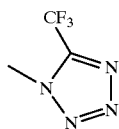

A halogenated compound of Formula (I) where $R_1$ is a bromine, chlorine or iodine atom can be converted by an Arbuzov reaction, preferably by treatment with diethyl phosphite in toluene at the boiling point of the reaction mixture, into a diethyl phosphonate of Formula (I) where $R_1$ is a —P(O) (OEt)$_2$.

A phosphonate of Formula (I) where $R_1$ is a —P(O) (OEt)$_2$ can be hydrolyzed by known methods, for example in the presence of trimethylsilyl iodide, to lead to a phosphonic acid of Formula (I) where $R_1$ is a —PO$_3$H$_2$ group.

The ketones that have been used in the preparation of the compounds of the invention have been prepared as follows:

6-bromo-3-coumarone is prepared in four steps from commercial 3-bromophenol. The first step consists of an O-alkylation of the 3-bromophenol by methyl bromoacetate. The saponification of the methyl 3-bromophenoxyacetate allows one to obtain 3-bromophenoxyacetic acid, which is converted into the acid chloride by the action of thionyl chloride. This is subjected to an intramolecular Friedel Craft acylation to yield 6-bromo-3-coumarone.

The preparation of 6-cyano-1-tetralone has been described in the prior art (C. Almansa et al., Synthetic Commun., 23, 2965, 1993). 6-methoxy-1-tetralone in the presence of aqueous hydrobromic acid leads to 6-hydroxy-1-tetralone which, in the presence of trifluoromethane sulfonic anhydride in pyridine allows one to obtain 6-trifluoromethane sulfonyl-1-tetralone. The action of potassium cyanide on the triflate previously obtained in the presence of nickel (0) allows one to obtain 6-cyano-1-tetralone.

The compounds of the invention exhibit very interesting properties on differentiation and cellular proliferation, that allow one to consider their use for therapeutic dermatological and cosmetic purposes. Among therapeutic uses, one may mention the treatment and the prevention of cancers of the solid tumor type such as cancers of the breast, the lungs, the prostate and the liver as well as the treatment and the prevention of skin diseases, such as psoriasis and acne.

In addition, molecular biology work reported below, has allowed definition of activity profiles of the compounds of the invention on retinoic receptors and certain transcriptional factors.

It has recently been suggested that RXR agonist compounds be used in the treatment of non-insulin dependent diabetes and inflammatory and immunitary diseases. As a consequence, the compounds of the invention are useful in the treatment of non-insulin dependent diabetes and inflammatory and immunitary diseases.

Hence, the invention also relates to the use of compounds of Formula (I) for the manufacture of pharmaceutical compositions useful in the treatment or the prevention of cancers as well as for the treatment of non-insulin dependent diabetes and inflammatory and immunitary diseases. They can also be used for the manufacture of cosmetic compositions useful in the treatment or the prevention of diseases of the skin.

As a medicine, the compounds of the invention are administered in the form of a pharmaceutical composition comprising at least said derivatives, in free form or in the form of a pharmaceutically acceptable salt, it association with a traditional vehicle or diluent. Theses compounds can also be administered in the form of pharmaceutically acceptable, hydrolyzable esters. By pharmaceutically acceptable esters, one means esters such as benzyl esters or substituted benzyl esters, and more particularly benzyl esters substituted with lower alkyl groups.

Such compositions, which also form part of the invention, can be presented in a form for administration by an enteral route, for example in the form of tablets, or for administration by a parenteral route, for example in the form of solutions or suspensions that can be injected by an intravenous or muscular route or for administration in the form of a nasal spray.

As a cosmetic, the compounds of the invention are administered in the form of a cosmetic composition comprising at least said derivatives, in free form or in the form of a pharmaceutically acceptable salt, in association with a traditional vehicle or diluent. Such compositions, which also form part of the invention, can be presented for administration by an enteral route, for example in the form of tablets, or for administration by a parenteral route, for example in the form of solutions or suspensions that can be injected by an intravenous or muscular route or for administration in the form of a nasal spray or advantageously for topical application in the form of creams, ointments, lotions, powders or gels.

The vehicles and diluents that may be used in association with the compounds of the invention are those generally used in this type of indication.

For the previous indications, the dose depends on the method of administration and the treatment desired. Satisfactory results are obtained when the derivative is administered at a daily dose of between 0.1 mg/kg and about 100 mg/kg. For man, the administration is carried out, for example, by the intravenous route, in a single dose per day or in fractionated doses up to several times per day, in the form of unitary doses containing a concentration of from 0.001% to about 0.01% of active substance.

ACTIVITIES OF THE COMPOUNDS OF THE INVENTION ON THE RETINOIC RECEPTORS AND CERTAIN TRANSCRIPTIONAL FACTORS

I) Models and Reference Molecules

The all trans retinoic acid (ttRA) and its stereo-isomers 9-cis, 11-cis and 13-cis bond themselves to and activate more or less selectively, intranuclear receptors called retinoic receptors. An important advance in the molecular action mechanism of the transduction signal of the retinoic acid has been established notably thanks to pioneering work by R. M. Evans et al. (Sciences, 1988, 240, 889–895).

The compounds of the invention of the retinoid or arotinoid type have different selectivity profiles with respect to the sub-types of receptors of the retinoic acid (RARs) and the retinoid X receptors (RXRs).

A large number of recent clinical results have shown that retinoic acid, certain of its isomers and derivatives forming the class of retinoids, are used for the treatment of diseases such as acne, psoriasis and certain cancers (U. Reichert et al., Pharmacology of Retinoids in the Skin, Karger AG Eds, Basel, 1989; M. S. Tallman et al, Retinoids in Cancer Treatment, J. Clin. Pharmacol., 1992, 32, 868–888; Warrell et al., N. Engl. J. Med., 1991, 324, 1385–1393).

These retinoids have also been evaluated in other therapeutic fields such as, for example, arthritis (Vinienti M. P. et al., Using Inhibitors of Metalloproteinases to treat Arthritis, Arthritis Rheumatoidism, 1994, 37, 1115–1126); dyslipidemia (Rottman et al., A RARE Element in the Apolipoprotein AI Gene Distinguishes Between Two Different Retinoic Acid Response pathways, Mol. Cell. Biol., 1991, 3814–3820); the prevention of HIV induced lymphopenia (Yang Y. et al., 9-cis RA Inhibits Activation Driven T-cell Apoptosis: Implications for Retinoid X Receptor Involvement in Thymocyte Development, Proc. Natl. Acad. Sci. USA, 1993, 90, 6170–6174). These therapeutic effects result from the capacity of the retinoic acid and of certain retinoids to control abnormal cellular situations by the modulation of the cellular growth, of the cellular differentiation and/or the apoptosis or programmed cellular death (The Retinoids, Biology, Chemistry and Medicine, M. B. Sporn, A. B. Roberts and D. S. Goodman, Raven Press Eds, 2nd ed, New York 1994). These regulations have been attributed for the large part to the formation of ligand(s)-receptor complexes. These proteins belong to the super-family of nuclear receptors and operate as dependent ligand transcription factors. These are the interactions which are responsible for the transcriptional activation and the associated physiological effects.

Using endogenic and synthetic ligands, this family has been classified into two series named RAR and RXR, each composed of three sub-types of receptors called $\alpha$, $\beta$ and $\gamma$. Furthermore, these retinoids have shown themselves capable of regulating the expression of other genes through an inhibitor effect of transcriptional factors like the complex AP-1 made up of the oncogenic proteins c-Fos and c-Jun. All these receptor proteins modulate the expression of certain genes by selective bonding, in dimer form, to specific regions of the DNA called RAREs (Retinoic Acid Response Elements, M. B. Sporn et al., p.319–349, D. J. Mangelsdorf et al., Proc. Natl. Acad. Sci. USA., 1991, 88, 3559–3563).

The RXR receptors function as homodimers or are able to heterodimerize themselves with the RAR receptors as well as with the other members of the super-family of intracellular receptors.

The all-trans retinoic acid (ttRA) is the natural ligand of the RAR receptors, while its 9-cis isomer (9-cis RA) is a ligand both for the RXR and RAR receptors in the form of homodimers and heterodimers (M. B. Sporn, page 5–178, X-K. Zhang et al, Homo-dimer formation of Retinoid X receptor induced by 9-cis RA, Nature, 1992, 358, 587–591, Heyman R. A. et al., 9-cis RA is a high affinity ligand for the retinoic receptor X, Cell, 1992, 68, 397–406, Levin A. A. et al., 9-cis RA stereo-isomer binds and activates the nuclear receptor RXR$\alpha$, Nature, 1992, 355, 359–361).

It has been shown that these receptors are significantly different: the primary structures of the bonding domains (amino-acid composition) are more than 80% different. Similarly, a different distribution of these sub-types of receptors is a function of the nature of the tissues. For example, the RARs are not expressed in the viscera, contrary to this the RXR$\alpha$ mRNA are the most abundant in the liver, the kidneys, the lungs, the intestine and the muscles.

The hormonodependent routes of the RARs can be activated by the specific RAR ligands which are linked to the RAR part of the RAR-RXR heterodimers, while specific RXR ligands show themselves incapable of activating these same routes by fixing themselves onto the RXR part. RXR ligands exhibit an activation synergy for genes responding to the all-trans RA when they are used in association with specific RAR ligands (Roy B. et al., Mol. Cell Biol., 1995, 15, 6481–6487). The RXRs form homodimers, in the presence of RXR ligands and regulate the transcription of genes which are distinct from those controlled by the RAR-RXR heterodimers (Zhang X-K. et al. quoted above).

Hence retinoids which are selective for the sub-types of receptors will be useful for a selective or independent control of the physiological routes mediated by these same sub-types. By way of comparison a panagonistic agent will be useful to control the physiological routes mediated by several of these sub-types. It appears that retinoids acting selectively on these sub-types will be able to increase the therapeutic efficacy and reduce the profile of secondary effects. A panagonistic agent is defined as an agent which links itself to and activates at least one of the receptors of the RAR sub-family and of the RXR sub-family. A true panagonistic agent activates all the members of the RAR and RXR sub-families.

The all-trans retinoic acid (ttRA), like its 13-cis isomer, has, at the time of any chronic treatment, a powerful effect of hypervitaminose, of mucocutaneous toxicity and of teratogenecity. Furthermore, ttRA is an inducer of its own metabolism which has the direct effect of rapidly reducing its therapeutic efficacy.

This is why, this invention aims to provide new compounds having greater chemical and metabolic stability and different activity profiles in relation to these sub-types of receptors linked to anti-tumoral activities and well established selective anti-proliferative activities. Such a strategy has lead to the formation of molecules which are:

RAR-RXR panagonistic
RAR or RXR selective
anti-AP-1 dissociating.

Through their property of co-activation of, the RAR proteins, RXR-selective retinoids constitute a new therapeutic advance. At doses where they are inactive themselves, they can increase the activity of RAR-selective retinoids, notably RARα, useful in the treatment (regression or remission) of cancers of the leukemia type, of solid tumors, more particularly cancers of the breast, the head and neck, but also in a more classical way in episodes of acne, severe acne and skin damaged by the sun. The administration of retinoids used in combination, can be concomitant or simultaneous. In this case, the spacing apart of the administration of the retinoids must not exceed a few hours, so that the RXR and RAR retinoids will be in blood concentrations such that the potentialization is effective.

1) Expression of RAR, RXR and RE Receptors as a Function of Cellular Lineages

The MCF-7 and HeLa cells are cultivated in DMEM with phenol red with 5% fetal calf serum added. The T47-D cells are cultivated in RPMI with 10% fetal calf serum added. The experimental tests are carried out in DMEM with phenol red with added fetal calf serum treated with dextran carbon at 3%. The cellular lineages transfected in a stable way, and stemming from MCF-7 and HeLa lineages, are established in accordance with the protocol described by D. Gagne et al., (J. Biolumin. Chemilumin., 1994, 9, 201–209). The experiments using the various retinoids are carried out sheltered from the light so as to prevent any isomerisation.

Table I below reports on the expression difference for the retinoic acid receptors and the receptor to the RE estrogens by the HeLa and MCF-7 cells (Titcomb M. W. et al., Mol. Endocrinol., 1994, 8, 870–877). The results in Table 1 are expressed in fentomoles of receptor per mg of proteins.

TABLE 1

| Type of receptor | HeLa | MCF-7 |
| --- | --- | --- |
| RE | not detected | expressed |
| RARα | 28 | 80 |
| RARβ | 9 | not detected |
| RARγ | 16 | 34 |
| RXRα | 50 | 12 |
| RXRβ | 28 | not detected |
| RXRγ | 9 | not detected |

2) Specificity of the Reference Molecules in Models of Transitory Transfections a) Chimerical receptors Gal4-RAR Studies of the transactivational specificity of the retinoids have been carried out by transitory transfection of HeLa cells. Two types of chimerical receptors can then be expressed by the cells. The plasmids Gal-RARα, Gal-RARβ and Gal-RARγ (J. Y. Chen et al., EMBO J., 1995, 14, 1187–1197) code for the chimerical receptors Gal4-RAR in which the domain of bonding to the DNA of the yeast protein Gal4 is merged with the E and F regions (regions containing the domain of bonding to the ligand and the activation function AF-2) of the receptors of retinoic acid. The C region (domain of bonding to the DNA) and the A and B regions (AF-1 activation domain) are suppressed.

These chimerical receptors activated by an agonist specifically stimulate the transcription of the gene of the luciferase present in a co-transfected plasmid ((17M)5-βG-Luc) where 17M is the response element of Gal4. The transcriptional co-operation between AF-1 and AF-2 does not exist with this type of receptor.

The use of reference molecules has allowed the validity of the GAL-RAR model to be verified in order to determine the specificity of agonist molecules: this GAL-RAR model translates the affinity of a compound for the domain of bonding to the RAR hormone. The arotinoid TTNPB, at concentration $10^{-8}$ M, is used as a maximum transactivation reference (100%) obtained with a synthetic agonist. Hence TTNPB and all-trans RA are good RAR agonists while Am580 behaves like a RARα specific molecule at a concentration of 10 nM. The compounds described as RXR specific (LGD1069 and LGD-CB14499) do not allow one to observe a good transactivation mediated by RAR. Table 12 below reports these results, where the activity of the compounds is expressed as a percentage of the activity measured for $10^{-8}$ M TTNPB.

The compound designated LGD1069 (Boehm M. F. et al., J. Med. Chem., 37, 2930–2941, 1994) corresponds to the following formula:

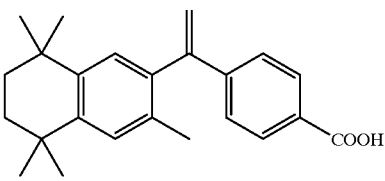

The compound designated LGD-CB14499 (Boehm M. F. et al., J. Med. Chem., 37, 2930–2941, 1994) corresponds to the following formula:

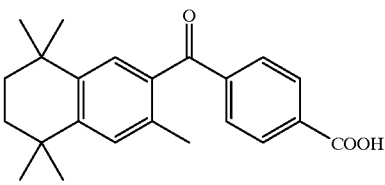

The compound designated Am580 is 4-[(5,6,7,8-tetrahydro-5,5,8,8-tetramethyl-2-naphthalenyl)carboxamido]benzoic acid (Shudo K. et al., J. Med. Chem., 1988, 31, 2182–2192).

TABLE 2

| | GAL4-RAR | | | |
| --- | --- | --- | --- | --- |
| Product | Concentration | RARα | RARβ | RARγ |
| ttRA | −8 | 82 | 104 | 106 |
| | −7 | 102 | 93 | 104 |
| | −6 | 108 | 92 | 111 |
| Am580 | −8 | 110 | 22 | 12 |
| | −7 | 102 | 77 | 64 |
| | −6 | 113 | 111 | 96 |
| TTNPB | −8 | 100 | 100 | 100 |
| | −7 | 101 | 116 | 94 |
| | −6 | 105 | 109 | 112 |
| LGD1069 | −8 | 0 | 1 | 1 |
| | −7 | 7 | 5 | 8 |
| | −6 | 21 | 22 | 29 |
| LGD-CB14499 | −8 | 1 | 0 | 0 |
| | −7 | 4 | 1 | 0 |
| | −6 | 17 | 9 | 13 | b) Chimerical receptors ERcassettes

The chimerical receptors RAR-ERcassettes have been described by Petkovitch et al. (Nature, 1987, 330, 444–450). The HeLa cells are co-transfected by a plasmid which codes for a retinoic receptor in which the C domain of bonding to the DNA is substituted by that of the receptor to RE estrogens, and a plasmid which places the expression of the luciferase under the control of an ERE (Element of Response to Estrogens). The expressed chimerical receptors are designated as RARα-ERcassette, RARβ-ERcassette, RARγ-ERcassette and RXRα-ERcassette. The A, B, D, E and F regions of the natural receptor are preserved as well as the transcriptional co-operation between the activation domains AF-1 and AF-2. These transitory transfection experiments follow the method of co-precipitation to calcium phosphate. The HeLa cells are co-transfected by 0.25 mg of plasmid coding for the chimerical receptor, 1 mg of reporter plasmid and 0.5 mg of expression vector CMV-β-galactosidase used as an internal control of transfection. 24 hours after the transfection, the cells are incubated for 16 hours with the different effectors.

In this type of chimerical receptor, the C domain of bonding to the DNA of RAR is substituted by that of the receptor to the RE estrogens. The protein obtained is close to the natural RAR receptor and preserves the transcriptional properties of the AF-1 and AF-2 domains. It modulates the transcription by means of an ERE. This RAR-ERcassette model allows one to observe a transcriptional response to a more physiological ligand.

The effect of the natural hormones (all-trans RA and 9-cis RA) is remarkable. These ligands induce an over-expression of luciferase in comparison to the induction brought about by a synthetic compound (TTNPB). This phenomenon is also observed for other responses (cf. notably results of transactivation on the HRLN models). This shows that the RAR-ERcassette constructions reflect a physiological context. The RARα specificity of Am580 is again verified for concentrations less than 10 nM. The profile defined in an RAR-ERcassette for the agonists RXR (LGD1069 and LGD-CB14499) differs from their GAL-RAR profile. In comparison to TTN-PB, their transcriptional power appears higher notably through the RARβ-ERcassette. This result can be explained by a heterodimerization of RAR-ERcassette with the endogenic RXR receptors expressed by the transfected HeLa cells. 1 μM LGD1069 permits a co-activation of RAR and RXR, bringing about an over-activation of the hetero-dimer in comparison with the specific RAR activation of TTNPB. The RAR-ERcassette model therefore indicates an RAR activity of a compound and also an RXR activity. Hence any panagonistic molecule causes a maximum transcription greater than that of TTNPB. This observation is confirmed by the fact that if a RAR specific molecule is associated with a RXR specific molecule, an over-expression of luciferase occurs. The use of the RAR-ERcassette construction thus permits one to visualize and to provide evidence for an RXR activity as reported in Table 3 below.

TABLE 3

RAR-Ercassettes

| Product | Concentration (Log M) | RARα (%) | RARβ (%) | RARγ (%) |
|---|---|---|---|---|
| ttRA | −9 | 65 | 93 | 86 |
|  | −8 | 127 | 128 | 114 |
|  | −7 | 249 | 270 | 122 |
|  | −6 | 443 | 475 | 189 |
| 9-cis RA | −9 | 7 | 16 | 11 |
|  | −8 | 60 | 94 | 56 |
|  | −7 | 187 | 212 | 108 |
|  | −6 | 348 | 369 | 157 |
| Am580 | −9 | 88 | 6 | 9 |
|  | −8 | 113 | 70 | 45 |
|  | −7 | 115 | 99 | 93 |
|  | −6 | 106 | 89 | 100 |

TABLE 3-continued

RAR-Ercassettes

| Product | Concentration (Log M) | RARα (%) | RARβ (%) | RARγ (%) |
|---|---|---|---|---|
| TTNPB | −9 | 52 | 93 | 66 |
|  | −8 | 100 | 100 | 100 |
|  | −7 | 119 | 104 | 97 |
|  | −6 | 123 | 116 | 112 |
| LGD1069 | −8 | 14 | 78 | 19 |
|  | −7 | 36 | 194 | 41 |
|  | −6 | 70 | 237 | 62 |
| LGD-CB14499 | −8 | 4 | 10 | 13 |
|  | −7 | 12 | 58 | 31 |
|  | −6 | 42 | 130 | 66 |

3) Effect of the Reference Retinoids on the Estrogen-induced Proliferation—Cellular Lineages MCF-7 and T-47D So as to test the anti-proliferation effect of the retinoids, growth experiments under oestrogenic conditions were carried out on cells MCF-7 and T-47D. These are the human estrogen-dependent mammary cancer cells which express the receptor to RE estrogens. The effect of the molecules is evaluated after 7 days of culture in oestrogenic conditions (estradiol $10^{-9}$ M) by dosing the cellular DNA. The cells are distributed in 24 well plates at a density of $2 \times 10^4$ cells per well. The tests with the different retinoids are carried out in triplicate and the culture medium is changed after 4 days of growth. The cellular DNA is measured by the method of 4,6-diamidino-2-phenylindole (C. F. Brunck et al., Anal. Biochem., 1979, 92, 497–500). The activity of the compounds is expressed as a percentage, 100% representing the quantity of DNA measured with $10^{-9}$ M estradiol.

Table 4 below shows the concentrations of retinoid required to inhibit by 50% the growth of MCF-7 and T-47D cells, or the percentage inhibition of growth at a concentration of 1 μM. The RAR specific molecules (TTNPB and Am580) exert a stronger inhibiting effect than the natural ligands (all-trans RA and 9-cis RA) and than LGD1069 (RXR agonist). These results confirm those reported by Dawson et al., Cancer Res., 1995, 55, 446–451, which have shown that RARα agonists are effective inhibitors of the growth of MCF-7 cells and that the affinity of retinoids for RARα is closely correlated to their anti-proliferation activity. At a concentration of $10^{-8}$ M, LGD1069 is RARα specific and exerts no effect whatsoever on the growth of MCF-7 and T-47D cells in estrogenic conditions.

TABLE 4

ANTI-PROLIFERATION EFFECT

| Product | T-47D $IC_{50}$ (nM) | MCF-7 $IC_{50}$ (nM) |
|---|---|---|
| ttRA | 39.1 | 14.1 +/− 10.3 |
| 9-cis RA | 25.1 +/− 1.4 | not determined |
| Am580 | 74% | 67% |
| TTNPB | 3.3 +/− 1.1 | 0.35 +/− 0.07 |
| LGD1069 | 20% | 33% |

Certain properties of the retinoids have been determined using more developed cellular models. These models consist of cellular lineages transfected in a stable fashion by recombinant plasmids which place the expression of the gene of the luciferase under the control of different nuclear response elements. The observed effects then correspond to physiological regulations and to an activity of endogenic receptors. The tests carried out in duplicate are described below for each of these models.

4) Transactivational Activity of the Reference Retinoids Mediated by the Receptors of Retinoic Acid—Cellular Lineages HRLN and HRL+N Transfected in a Stable Fashion The cellular lineages HRLN and HRL+N allow one to study the activation of an RARE by endogenic receptors using ligands at physiological concentrations. These lineages derive from HeLa cells transfected in a stable fashion by a reporter gene which places the expression of the gene of the luciferase under the control of a nuclear response element RARE ($RARE_3$-tk-Luc). The HeLa cells express all the known receptors of the retinoic acid (RARα,β,γ and RXRα,β,γ) with a predominance of RARα and RXRα. The response element RARE used for the HRLN cells corresponds to the sequence of the natural gene of the RARβ receptor (GGTTCAnnnnnAGTTCA). The HRL+N cells comprise the sequence GAGTGAnnnnnCGGTGA.

a) HRLN lineage

This lineage comprises the response element RARE of the natural gene of the RARβ receptor which controls the expression of the gene of the luciferase. ttRA and 9-cis RA induce a dose-dependent activation. An over-activation in comparison to TTNPB is observed at high concentration (1 μM), comparable to that observed with the ERcassette constructions. A co-activation of RAR and of RXR at the level of the hetero-dimer is certainly implied.

The results relating to TTNPB and Am580 indicate the activation induced specifically by the RAR receptors. The $EC_{50}$ values for these two molecules are similar. Am580 induces a transactivation mediated by RARα and TTNPB by RARα,γ as the use of the antagonist RARα Ro 41-5253 shows (Apfel, C. et al., PNAS, USA, 1992, 89, 7129–7133) which totally abolishes the response of Am580 and partially abolishes that of TTNPB. However RARα appears as the predominant receptor for the transactivation in the HeLa cells. The RARα specific ligand LGD1069 transactivates with an $EC_{50}$ of –10 nM, which corresponds to its RXR activity. The HRLN lineage allows clearer evidence to be given of a physiological RAR activity of the compounds, but a weak RXR activity is observed. Table 5 below reports these results where 100% expression corresponds to the induction caused by TTNPB $10^{-8}$ M. The $EC_{50}$ values are determined from results obtained with a range of concentrations going from 1 nM to 1 μM.

TABLE 5

HRLN TRANSACTIVATION

| Product | E max % | $EC_{50}$ (nM) |
|---|---|---|
| ttRA | 208 | 2.5 +/– 4 |
| 9-cis RA | 196 | not determined |
| Am580 | 104 | 0.10 +/– 0.006 |
| TTNPB | 100 | 0.55 +/– 0.72 |
| LGD1069 | 73 | 9.4 +/– 6.3 |
| LGD-CB14499 | 30 | not determined | b) HRL+N lineage

The transactivation results obtained with the HRL+N lineage are comparable to those obtained with the HRLN lineage for the RAR agonist molecules (TTNPB and Am580) and the natural ligands (ttRA and 9-cis RA). The RXR agonists (LGD1069 and LGD-CB14499) induce a stronger transactivation with the HRL+N cells and LGD1069 1 μM is more effective than the RAR specific molecules. Furthermore, the association of an RAR agonist and an RXR agonist (for example TTNPB+LGD-CB14499, FIG. 1 in the Appendix) permits a better transactivation than that brought about by either molecule used separately. The HRL+N lineage allows one to visualize a co-activation of the RAR and RXR receptors at the level of the RAR-RXR hetero-dimer. Hence, LGD1069 1 μM having a RAR activity at this concentration behaves as a panagonistic molecule. This result is to be correlated to the over-activation induced by the RXR agonist molecules with the RAR-ERcassettes. The HRL+N lineage allows clear evidence to be given of an RAR and RXR activity of the molecules. These results are reported in Table 6 below where the transcriptional activity of the products is expressed as a percentage, 100% corresponding to the level of activity measured in the presence of TTNPB $10^{-8}$ M.

TABLE 6

HR + N TRANSACTIVATION

| Product ($10^{-6}$ M) | Emax (%) |
|---|---|
| ttRA | 225 |
| Am580 | 99 |
| TTNPB ($10^{-8}$ M) | 100 |
| LGD1069 | 131 |
| LGD-CB14499 | 94 |

FIG. 1 in the Appendix shows the over-activation induced by a RXR selective molecule in the presence of an RAR specific aconist on the HRL+N model.

5) Anti-AP-1 Effect of Reference Retinoids on Estrogen-dependent Cells Activated by TPA—MTLN Cellular Lineage The anti-factor AP-1 transrepressor effect of retinoids is determined using the MTLN lineage, coming from MCF-7 cells transfected in a stable fashion by a vector $p(TRE)_3$-tk-Luc which places the expression of the gene of luciferase under the control of TPA (12-O-tetradecanoyl-phorbol-13-acetate). TPA activates the AP-1 complex formed from proteins of the family of nuclear proto-oncogenes (c-Jun and c-Fos). This MTLN lineage permits the study of the relationship existing between the estrogenic routes and AP-1 (M. E. Astruc et al., Endocrinology, 1995, 136, 824–832), and to show the dissociation between the transactivator activity and the anti-AP-1 effect of retinoids from syntheses (J. Y. Chen et al., EMBO J., 1995, 14, 1187–1197). The experiments ware made with the MTLN cells activated by $10^{-7}$ M TPA.

The results reported in Table 7 below show that the 3 types of retinoic acid receptors expressed by the MCF-7 cells (RARα,γ and RXRα) mediate an inhibitor effect of the AP-1 route. The use of the selective RARα antagonist Ro 41-5253 does not allow the inhibition induced by TTNPB to be totally lifted, which indicates that the activation of RARγ mediates an anti-AP-1 effect. The activation by an RARα agonist (Am580 10 nM) or RXRα (LGD1069 and LGD-CB14499) also causes an inhibition of the AP-1 route. The association of an RAR specific molecule and an RXR specific molecule provokes a strong ant-AP-1 inhibiting effect, there is an additive effect between the to inhibition routes. From its panagonistic profile at 1 μM, LGD1069 appears as the most effective compound tested in this model.

TABLE 7

ANTI-AP-1 EFFECT

| Product | Concentration (Log M) | Inhibition (%) |
|---|---|---|
| ttRA | −8 | 22–33 |
|  | −7 | 28–44 |
| 9-cis RA | −8 | 30–37 |
| Am580 | −8 | 40–46 |
|  | −7 | 41–48 |
| TTNPB | −8 | 26–53 |
|  | −7 | 29–54 |
| LGD1069 | −8 | 18–29 |
|  | −7 | 48–62 |
| LGD-CB14499 | −7 | 17–30 |

The effect of the compounds on the MTLN cells activated by $10^{-7}$ M TPA is expressed as a percentage. 100% represents the maximum level of activity measured with TPA which is 5 to 6 times greater than the base activity of the cells. The inhibitive properties of the products are calculated after deduction of the base activity of the cells. The percentages reported correspond to a range of inhibitions determined from several experiments.

Figure 2:
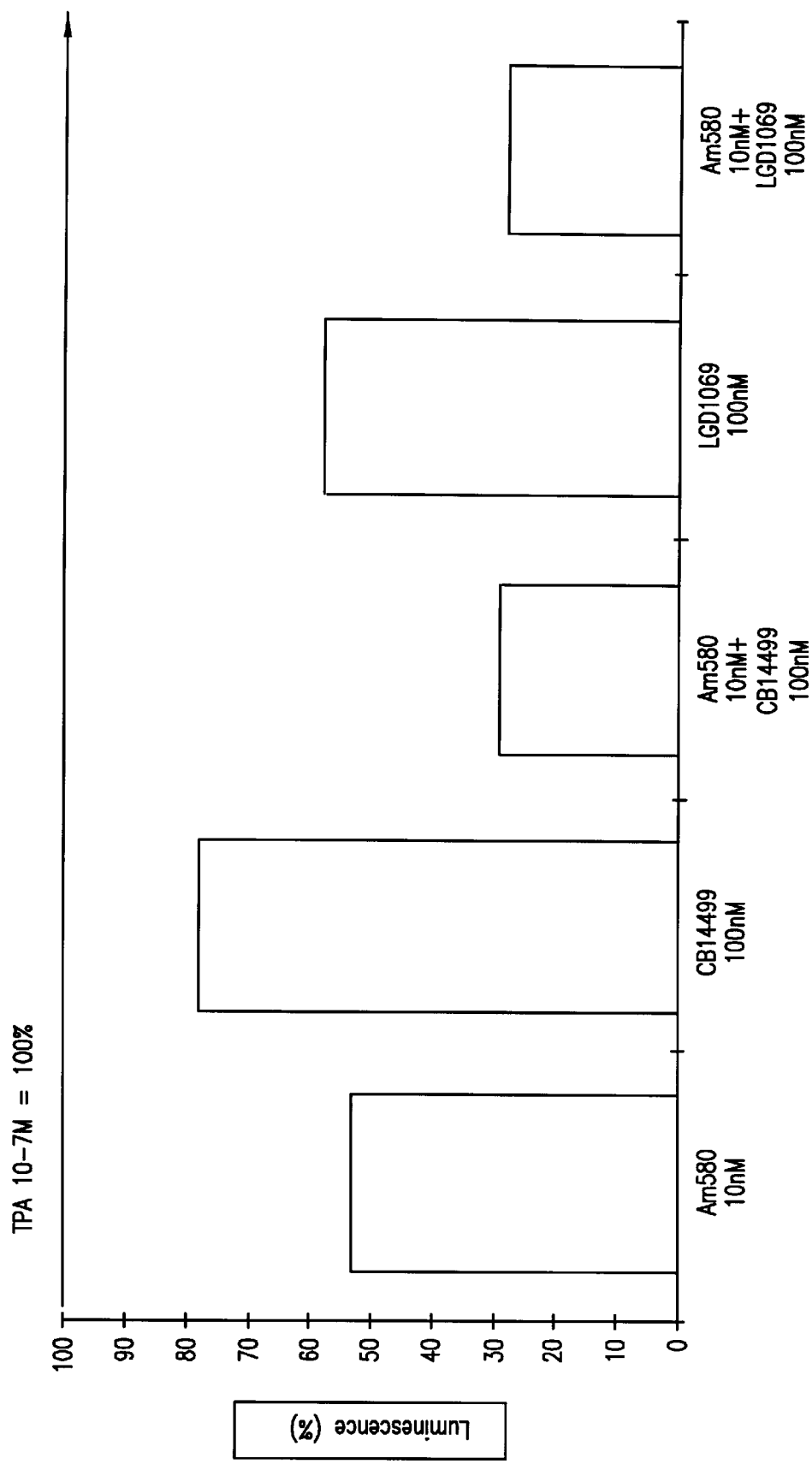

FIG. 2 in the Appendix shows the additive nature of the anti-AP-1 inhibitor effect on the MTLN lineage of an RXR agonist and a selective RAR agonist.

6) Anti-estrogenic Effect of the Reference Retinoids on the Estrogen-dependent Cells Activated by Estradiol—MELN Lineage MCF-7 cells express RARα,γ and RXRα. The transfection of MCF-7 cells by an estrogen-dependent gene (ERE-βGlob-Luc) has permitted the establishment of the MELN cellular lineage, used to determine the anti-oestrogenic activity of the retinoids. These cells contain the gene of the luciferase under the transcriptional control of the promoter of the βGlobine and of the response element ERE isolated from the gene of chicken vitelogenine A2. The experiments are carried out with MELN cells activated by $10^{-9}$ M estradiol. The level of base activity of the MELN cells is obtained with the anti-estrogen 1 μM 4-OH-tamoxifen (hydroxytamoxifen). This level is always from 8 to 10 times lower than the maximum reference activity measured in the presence of $10^{-9}$ M estradiol which represents 100%. All-trans RA reduces the cellular growth and the expression of estrogen-dependent genes (E. Demirpence et al., Cancer Res., 1994, 54, 1458–1464), which this MELN lineage allows one to verify.

The RAR selective molecules (Am580 and TTNPB) induce an inhibition of the order of 40%. Am580 at a specific RARα concentration (19 nM) permits maximum inhibition, which indicates that RARα mediates the anti-estrogenic effect in-the MCF-7 cells. The use of the RARα antagonist Ro 41-5253 raises the inhibitor effect of Am580 and also of TTNPB which, under these conditions, preserves an RARγ activity and loses its RARα activity. The RXR selective compounds (LGD1069 and LGD-CB14499) are inactive. The activation of RXR is therefore not implied in the inhibition of the estrogenic route by the retinoids in the MCF-7 cells.

These results are reported in Table 8 below, they are perfectly correlated with estrogen-induced cellular proliferation experiments. The association of an RAR specific agonist and an RXR specific agonist does not allow one to observe an inhibitor effect greater than that exerted by the RAR agonist alone.

TABLE 8

ANTI-OESTROGENIC EFFECT

| Product | Concentration (Log M) | Inhibition (%) |
|---|---|---|
| ttRA | −7 | 35 |
| 9-cis RA | −7 | 35 |
| Am580 | −8 | 36–51 |
| TTNPB | −8 | 30–41 |
| LGD1069 | −8 | 0 |
|  | −7 | 0 |
| LGD-CB14499 | −7 | 0 |
|  | −6 | 0 |

The effect of the products tested on the cells activated by $10^{-9}$ M estradiol is expressed as a percentage, the level of base activity being deducted.

6) Conclusion

The reference molecules have allowed one to show the effectiveness and the complementary nature of the different models used and lead to the following conclusions:

chimerical constructions GAL-RAR and RAR-ERcassette allow the determination of the RAR agonist profile of molecules, but also an RXR agonist activity with RAR-ERcassette, the HRLN lineage mainly conveys the activity of a compound mediated by endogenic RARα, the HRL+N lineage also provides evidence of an RXR agonist activity of the retinoids, the anti-estrogenic effect of the retinoids (estrogen-induced cellular proliferation and MELN lineage) is mediated by RARα, the anti-AP-1 effect is mediated in the MCF-7 cells (MTLN lineage) by RARα, RARγ and RXRα, and an additive effect exists between the RAR and RXR routes.

II—Activity of the Compounds of the Invention

1) Specificity of the Compounds of the Invention

The study of the selectivity of the compounds was carried out with the RAR-ERcassette chimerical receptors model. All the compounds tested are inactive or are weak transactivators with RARα. The products, that include a tetrazole are inactive (CB02981) or weakly active (CB23804, CB99811 and CB94083) on the three types of RAR receptors and are not therefore RAR agonists. The same result is observed for molecules whose ring is made up of 6 carbon atoms (CB66049 and CB80830).

Table 9 below reports these results, where 100% represents the transactivation measured for each type of receptor with TTNPB $10^{-8}$ M. The compounds were tested at the concentration of 1 μM. On one and the same line in the Table, the cis (Z) compound represents the isomeric structure of the trans (E) compound.

TABLE 9

| | | | RAR-ERcassettes | | | |
|---|---|---|---|---|---|---|
| (E) trans compound | RARα (%) | RARβ (%) | RARγ (%) | (Z) cis compound | RARα (%) | RARβ (%) | RARγ (%) |
| CB23804 | 4 | 28 | 19 | CB02981 | 4 | 7 | 0 |
| CB78937 | 18 | 65 | 93 | CB27871 | 29 | 36 | 67 |
| CB40341 | 14 | 75 | 79 | CB75403 | 12 | 65 | 68 |
| CB66049 | 0 | 0 | 8 | CB80830 | 2 | 0 | 1 |
| CB99811 | 3 | 11 | 14 | CB94083 | 4 | 14 | 18 |
| CB52809 | 5 | 0 | 13 | — | | | |
| CB93128 | 16 | 148 | 110 | — | | | |

As Table 9 and Table 10 below indicate, compounds having a ring of 5 carbon atoms and a carboxyl group have a certain interest. CB78937, CB40341 and CB75403 induce transactivation mediated by RARβ and by RARγ that is significant at a concentration of 1 μM and are inactive on RARα. These molecules have RARβ,γ specificity. Furthermore, CB75403 induces the same level of transactivation through the intermediary of RARβ at 0.1 μM and at 1 μM and also at 3 μM, which indicates that this molecule exhibits a strong affinity for RARβ but remains a partial agonist. CB93128 is also a RARβ,γ selective agonist. This compound is capable of completely activating RARγ at 1 μM and over-activates RARβ in comparison with the activation caused by TTNPB. This over-activation shows itself as an RXR activity.

TABLE 10

| | RAR-Ercassettes | | | |
|---|---|---|---|---|
| Product | Concentration (Log M) | RARα (%) | RARβ (%) | RARγ (%) |
| TTNPB | −8 | 100 | 100 | 100 |
| Am580 | −9 | 88 | 6 | 9 |
| | −8 | 113 | 70 | 45 |
| | −7 | 115 | 99 | 93 |
| | −6 | 106 | 89 | 100 |
| CB75403 | −7 | 3 | 68 | 40 |
| | −6 | 12 | 65 | 68 |
| CB93128 | −7 | 8 | 80 | 65 |
| | −6 | 16 | 148 | 110 |

2) Effect of the Compounds of the Invention on the Estrogen-induced Proliferation—Cellular Lineages MCF-7 and T-47D The effect of the retinoids on the growth of MCF-7 and T-47D cells is evaluated after 7 days of culture in the presence of $10^{-9}$ M estradiol by dosing the cellular DNA. The CB02981 molecule, which is inactive in RAR transactivation, exerts no effect whatsoever on the estrogen induced proliferation of the MCF-7 and T-47D cells.

3) Transactivational Activity of the Compounds of the Invention Mediated by the Receptors of the Retinoic Acid—Cellular Lineages HRLN and HRL+N a) HRLN lineage The transactivation results obtained with the HRLN lineage are correlated with the specificity results (RAR-ERcassette model). No molecule at 1 μM allowed transactivation comparable to that induced by the reference molecule TTNPB. The compounds that include a tetrazole or a ring of 6 carbon atoms are slightly active (CB23804) or inactive (CB02981, CB66049, CB80830), which is in agreement with their activity in a RAR-ERcassette model. The carboxylated products (CB78937, CB40341, CB27871 and CB93128) induce a partial transactivation that corresponds to their RARβ,γ activity. Table 11 reports the results obtained where 100% corresponds to the transactivation induced by $10^{-8}$ M TTNPB.

TABLE 11

| | TRANSACTIVATION HRLN | | |
|---|---|---|---|
| Product trans (E) | Transactivation at 1 μM (%) | Product cis (Z) | Transactivation at 1 μM (%) |
| CB23804 | 15 | CB02981 | 0 |
| CB78937 | 25 | CB27871 | 27 |
| CB40341 | 30 | CB75403 | not determined |
| CB66049 | 0 | CB80830 | 4 |
| CB99811 | not determined | CB94083 | not determined |
| CB52809 | 0 | — | |
| CB93128 | 51 | | |

2) HRL+N lineage

The use of the HRL+N model confirms the results obtained with the HRLN cells. As shown in Table 12 below, CB02981 does not cause transactivation mediated by RAR and RXR. In association with a selective RAR agonist, the compounds tested do not induce over-activation with the exception of CB93128. Only this product appears to show RXR activity (over-activation observed with a RARβ-ERcassette).

TABLE 12

| HRL − N TRANSACTIVATION | |
|---|---|
| Product | Transactivation at 1 μM (%) |
| TTNPB | 100 |
| CB02981 | 0 |
| CB75403 | 18 |
| CB94083 | 13 |

4) Anti-AP-1 Effect of the Compounds of the Invention on Estrogen-dependent Cells Activated by TPA—MTLN Cellular Lineage The influence of the compounds CB02981 and CB75403 at the concentration of 1 μM on the AP-1 route in the MCF-7 cells was determined with the MTLN model. The use of the reference molecules has shown that all the retinoic acid receptors expressed by the MCF-7 cells (RARα,γ and RXRα) mediate an anti-AP-1 effect. CB75403 causes inhibition of the order of 30%, which corresponds to the RARγ activity observed for this molecule. CB02981 shows very interesting activity. This compound, incapable of inducing a transactivation mediated by RAR, exerts an anti-AP-1 inhibiting effect of the order of 20% on the MTLN cells and exhibits a dissociating profile. Furthermore, in association with a RXR agonist, an additive effect of the inhibiting effects of the two molecules is observed.

Figure 3:
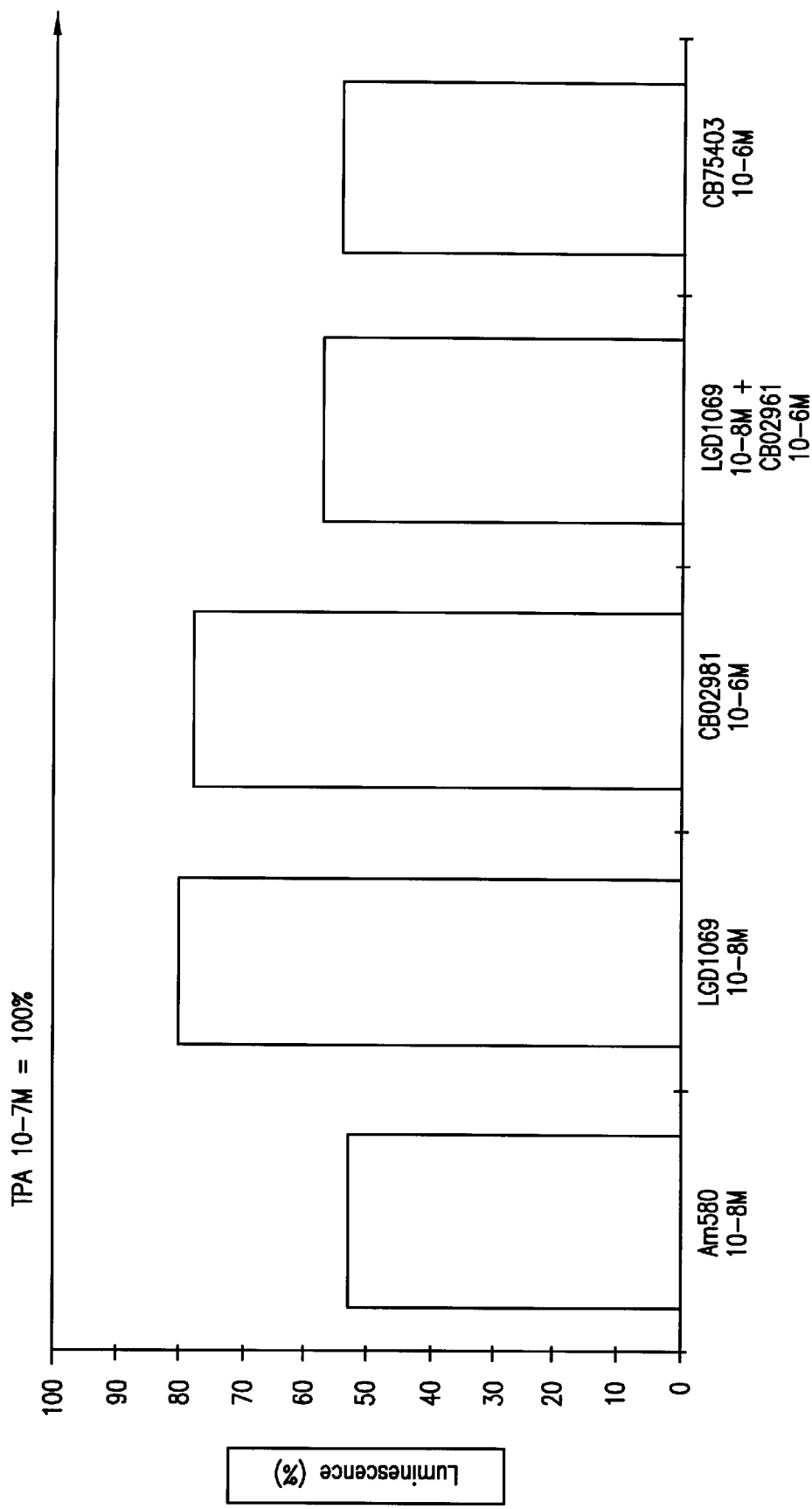

FIG. 3 represents the effect of compounds CB02981 and CB75403 on the MTLN lineage and the additive effect of the effects of CB02981 and a selective RXR agonist.

5) Anti-estrogenic Effect of the Compounds of the Invention on the Estrogen-dependent Cells Activated by Estradiol—MELN Lineage As reported in Table 13 below, the influence of the compounds at 1 μM on the expression of a gene controlled by an ERE was determined with the MELN model. No tested compound exerted any transrepressor effect which corresponds to their incapacity to mediate a transactivation through the intermediary of RARα.

ANTI-ESTROGENIC EFFECT

| Product trans (E) ($10^{-6}$ M) | Inhibition (%) | Product cis (Z) ($10^{-6}$ M) | Inhibition (%) |
|---|---|---|---|
| CB23804 | 0 | CB02981 | 0 |
| CB78937 | 4 | CB27871 | not determined |
| CB40341 | not determined | CB75403 | 0 |
| CB66049 | not determined | CB80830 | 2 |
| CB52809 | 0 | — | |

6) Conclusion

The work reported above shows the interesting properties of the compounds of the invention. Among these compounds, the molecules that include a carboxyl group and a ring of 5 carbon atoms are RARβ,γ specific. The conformational constraint present in these structures appear to be unfavorable to RARα activity and are directed towards RARβ,γ selectivity (CB40341, CB75403, CB78937). The presence of the ring causes a loss of RXR transcriptional activity. However, despite its transcriptional inactivity, CB02981 is a dissociating compound and causes inhibition of the AP-1 ring. The association of CB02981 and a RXR agonist can prove itself to be effective to provide potential for an anti-AP-1 effect. CB93128 has an original profile in that it is capable of activating RARβ, RARγ and RXR.

Other characteristics and advantages of the invention will become apparent on reading the examples which follow relating to the preparation and the analysis of reference compounds and derivatives of the invention, it being understood that these examples should not be interpreted as tending to reduce the scope of the claims.

EXAMPLE 1

Preparation of (E) 3-[2-(5,6,7,8-tetrahydro-5,5,8,8-tetramethyl)naphthalenylmethylene]-dihydro-benzo[b]furane-5-carboxylic acid, (CB93128)

1) Methyl 3-bromophenoxyacetate

A solution of 3-bromophenol (17.3 g, 100 mmol) in 30 ml of THF is added at ambient temperature to a 50% solution of sodium hydride dispersed in mineral oil (5 g, 125 mmol) in 50 ml of anhydrous THF. The mixture was stirred at ambient temperature for 30 minutes before successively adding a solution of methyl bromoacetate (10.4 ml, 110 mmol) in 33 ml of anhydrous THF and sodium iodide (3.75 g, 25 mmol). The reaction medium is stirred for 30 minutes at ambient temperature and then treated with 30 ml of water at 0° C. The raw product is purified by chromatography on silica (eluent petroleum ether:ether 100:10). 19.66 g of methyl 3-bromophenoxyacetate is obtained (yield=80%).

M. Pt. (° C.)=39.

NMR¹H 200 MHz (CDCl₃): 3.75 (s, 3H, MeO); 4.57 (s, 2H, CH₂—O); 6.75–6.85 (m, 1H, ArH); 7.00–7.25 (m, 3H, ArH).

2) 3-bromophenoxyacetic acid.

At 0° C., lithium hydroxide monohydrate (8.41 g, 0.2 mol) is added to a solution of methyl 3-bromophenoxyacetate (19.66 g, 80 mmol) in solution in 100 ml of a water-THF mixture (3:1). Agitation is continued for 15 minutes at 0° C. and then the mixture is acidified by a 3N aqueous solution of hydrochloric acid. It is extracted with ether, dried over MgSO₄, filtered and evaporated. 18.21 g of 3-bromophenoxyacetic acid is obtained (yield=98%).

M.Pt. (° C.)=108.

NMR¹H 200 MHz (CDCl₃): 4.70 (s, 2H, CH₂—O); 6.80–6.90 (1H, ArH); 7.05–7.10 (m, 1H, ArH); 7.15–7.20 (m, 2H, ArH); 9.40–9.05 (m, 1H, mobile H).

3) 6-bromo-3-coumarone.

Thionyl chloride (5 ml, 70 mmol) is added at ambient temperature to 3-bromophenoxyacetic acid (5.77 g, 25 mmol). The reaction mixture is brought to reflux for 2 hours. After returning to ambient temperature, it evaporates and the acid chloride is used. The 3-bromophenoxyacetyl chloride previously obtained is dissolved in dichloromethane (150 ml) and added to a solution of aluminum chloride (6.7 g, 50 mmol) in 50 ml of dichloromethane. The reaction medium is stirred at ambient temperature for 30 minutes and then poured into a an equal volume water-ice mixture (400 ml). The mixture is extracted with dichloromethane, dried over MgSO₄ filtered and evaporated. The raw product is purified by flash chromatography on silica (eluent petroleum ether ether=100:10). 0.96 g of 6-bromo-3-coumarone is obtained (yield=18%) of formula:

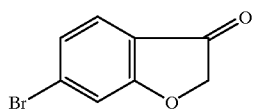

M.Pt. (° C.)=124.

NMR¹H 200 MHz (CDCl₃): 4.65 (s, 2H, CH₂—O); 7.10–7.25 (m, 1H, ArH); 7.45–7.60 (m, 2H, ArH).

4) (E) 5-bromo-[2-(5,6,7,8-tetrahydro-5,5,8,8-tetramethyl) naphthalenylmethylene]-dihydrobenzo[b]furane.

At –70° C. a 1M solution of tBuOK in THF (12.2 ml, 12.2 mmol) is added to a solution of (5,6,7,8-tetrahydro-5,5,8,8-tetramethyl-2-naphthalenyl)-6-methyl-triphenyl-phosphonium bromide (6 g, 11.06 mmol) in 16 ml of THF. Agitation is continued at –70° C. for 1 hour before adding 6-bromo-3-coumarone (1.18 g, 5.53 mmol) in 10 ml of THF at this temperature. The reaction medium is brought to ambient temperature and the agitation is continued for 2.5 hours. Then the mixture is hydrolyzed at 0° C. by a 3N solution of HCl (20 ml). After returning to ambient temperature, it is extracted with ether, dried over MgSO₄, filtered and the solvents evaporated. The raw product is purified by flash chromatography on silica (eluent:petroleum ether). 180 mg of (E) 5-bromo-[2-(5,6,7,8-tetrahydro-5,5,8, 8-tetramethyl)naphthalenylmethylenel-dihydro-benzo[b] furane (overall yield=8%) of formula:

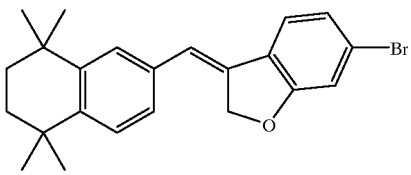

NMR¹H 200 MHz (CDCl$_3$): 1.25 (s, 6H); 1.30 (s, 6H); 1.65 (s, 4H); 4.95 (s, 2H); 6.95–7.10 (m, 2H),; 7.20 (s, 1H); 7.30 (s, 2H); 7.35 (s, 1H); 7.60 (s, 1H).

MS (m/z, % intensity): 398 (36%); 397 (14); 384 (44); 383 (86); 381 (81); 211 (97); 209 (100).

5) (E) 5-cyano-[2-(5,6,7,8-tetrahydro-5,5,8,8-tetramethyl)-naphthalenylmethylene]-dihydro-benzo[b]furane At ambient temperature, copper cyanide (48 mg, 5.81 mmol) is added to a solution of (E) 5-bromo-[2-(5,6,7,8-tetrahydro-5,5,8,8-tetramethyl)naphthalenyl-methylene]-dihydro-benzo[b]furane (180 mg, 0.45 mmol) in 1.7 ml of anhydrous DMF. The reaction medium is brought to reflux for 24 hours. After returning to ambient temperature, the reaction mixture is diluted with ether (50 ml) and filtered on celite. The organic phase is washed with a saturated aqueous solution of NaHCO$_3$ (3×20 ml) and then dried over MgSO$_4$, filtered and evaporated. The raw product is purified by flash chromatography on silica (eluent petroleum ether:ether= 100:5). 50 mg of (E) 5-cyano-[2-(5,6,7,8-tetrahydro-5,5,8,8-tetramethyl)-naphthalenyl-methylene]-dihydro-benzo[b]furane (yield=32%) is obtained of formula:

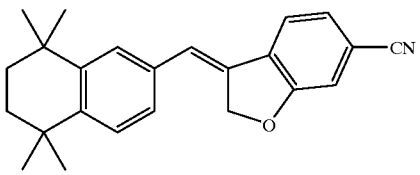

NMR¹H 200 MHz (CDCl$_3$): 1.20 and 1.25 (2s, 12H, 5,5,8,8-Me); 1.65 (s, 4H, 6.7-CH$_2$); 3.95 (s, 2H, CH$_2$—O); 6.90–7.00 (m, 2H); 7.40–7.45 (m, 2H); 7.50 (s, 1H); 7.52 (s, 1H); 7.75 (s, 1H).

6) (E) 3-[2-(5,6,7,8-tetrahydro-5,5,8,8-tetramethyl)-naphthalenylmethylene]-dihydro-benzo[b]furane-5-carboxylic acid, (CB93128)

A solution of (E) 5-cyano-[2-(5,6,7,8-tetrahydro-5,5,8,8-tetramethyl)-naphthalenyl-methylene]-dihydro-benzo[b]furane (50 mg, 0.14 mmol) in ethanolic potassium hydroxide (0.1 g, 1.7 mmol; H$_2$O 0.5 ml, EtOH 3 ml) and heated at reflux under magnetic stirring for 15 hours. The ethanol is evaporated in a rotary evaporator, taken up again in water (10 ml), acidified with 3N HCl, extracted with diethyl ether (3×50 ml), the ether phase dried over MgSO$_4$, filtered and evaporated. The raw product is purified by preparative HPLC (eluent: MeOH H$_2$O=90:10+0.1% of TFA). 12.5 mg of (E) 3-[2-(5,6,7,8-tetrahydro-5,5,8,8-tetramethyl) naphthalenyl-methylene]-dihydro-benzo[b]furane-5-carboxylic acid, (CB93128) is obtained (yield=25%) of formula:

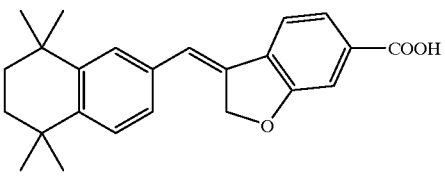

M.Pt. (° C.)=178–181.
NMR¹H 200 MHz (CDCl$_3$): 1.03 and 1.24 (2s, 12H, 5,5,8,8-Me); 1.65 (s, 4H, 6,7-CH$_2$—); 3.97 (s, 2H); 6.99 (d, 1H, J 8 Hz); 7.19 (s, 2H); 7.45–7.55 (m, 2H); 7.96 (d, 1H, J 8 Hz); 8.21 (s, 1H); 8.16–10.2 (m, 1H, mobile H).
MS (m/z, % intensity): 362 (56%); 348 (53); 347 (94); 175 (100).
MSHR EI 70 eV: M$_{tr}$=362.1881 for C$_{24}$H$_{26}$O$_3$ M$_{th}$=362.1882.
HPLC Column Waters HR C$_{18}$, 8×100 mm, 6 μ, detector UV Waters 486 to 260 nm, flow rate 3 ml/min, eluent MeOH:H$_2$O=90:10+0.1% of TFA, acid (CB93128) tr=3.81 min 99.6%.

EXAMPLE 2

Preparation of (Z) and (E) 1-[2-(5,6,7,8-tetrahydro-5,5,8,8-tetramethyl)naphthalenyl-methylene)-1,2,3, 4-tetrahydronaphthalene-6-carboxylic acids (CB80830 and CB66049)

1) (Z) and (E) 6-cyano-1-[2-(5,6,7,8-tetrahydro-5,5,8,8-tetramethyl)naphthalenylmethylene]-1,2,3,4-tetrahydronaphthalenes At −70° C. a molar solution of tBuOK in THF (6.1 ml, 6.1 mmol) is added to a solution of (5,6,7,8-tetrahydro-5,5,8,8-tetramethyl-2-naphthalenyl)-6-methyl-triphenyl-phosphonium bromide (3 g, 5.52 mmol) in 8 ml of THF. Agitation is continued at −70° C. for 1 hour before adding 6-cyano-1-tetralone (0.78 g, 4.6 mmol) in 7 ml of THF at this temperature. The reaction medium is brought to ambient temperature and the agitation is continued for 5 hours. After returning to ambient temperature, the reaction mixture is poured into 100 ml of a equivolume ice-water mixture. It is extracted with ether, dried over MgSO$_4$, filtered and the solvents evaporated. The raw product is purified by flash chromatography on silica (eluent:petroleum ether:diethyl ether=100:5). 600 mg of the mixture of (Z) and (E) 6-cyano-1-[2-(5,6,7,8-tetrahydro-5,5,8,8-tetramethyl)naphthalenyl-methylene]-1,2,3,4-tetrahydronaphthalenes (yield=37%). The precipitation of this mixture in pentane allows one to isolate 200 mg of pure (E) isomer and 330 mg of the (E) and (Z) mixture, enriched in (Z).

Isomer (E):

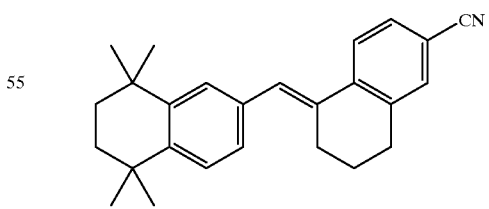

M.Pt. (° C.)=144.
NMR¹H 200 MHz (CDCl$_3$): 1.29 (s, 12H, 5,5,8,8-Me); 1.69 (s, 4H, 6,7-CH$_2$); 1.75–1.90 (m, 2H); 2.75–2.90 (m, 4H); 7.06 (s, 1H, vinyl H); 7.15 (dd, 1H, ArH, J 2Hz, J 8 Hz); 7.28 (s, 2H); 7.32–7.45 (m, 2H, ArH); 7.72 (d, 1H, ArH, J 8 Hz).

Isomer (Z):

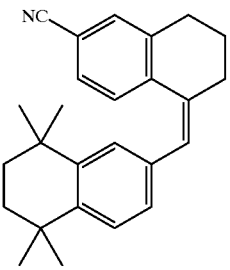

NMR¹H 200 MHz (CDCl₃): 1.08 and 1.24 (2s, 12H, 5,5,8,8-Me); 1.62 (s, 4H, 6,7-CH₂); 1.95–2.10 (m, 2H); 2.45–2.55 (m, 4H); 6.50 (s, 1H, vinyl H); 6;92 (d, 1H, ArH, J 8 Hz); 7.05–7.15 (m, 1H, ArH); 7.32 (dd, 1H, ArH, J 2 Hz, J 8 Hz); 7.45 (m, 1H, ArH).

2) (Z) and (E) 1-[2-(5,6,7,8-tetrahydro-5,5,8,8-tetramethyl)naphthalenylmethylene]-1,2,3,4-tetrahydro-naphthalene-6-carboxylic acids (CB80830 and CB66049).

At ambient temperature, potassium hydroxide (1.56 g, 27.9 mmol) of potassium hydroxide is added to the mixture of (Z) and (E) 6-cyano-1-[2-(5,6,7,8-tetrahydro-5,5,8,8-tetramethyl)-naphthalenylmethylene]-1,2,3,4-tetrahydronaphthalenes (330 mg, 0.93 mmol) in solution in 3 ml of THF, 1 ml of water and 2 ml of ethanol. The reaction mixture is brought to reflux under magnetic stirring for 36 hours. After returning to ambient temperature the mixture is evaporated, taken up again in water (10 ml), acidified with 3N HCl, extracted with diethyl ether (3×50 ml), the ether phase dried over MgSO₄, filtered and evaporated. The raw product is purified by preparative HPLC (eluent: MeOH:H₂O=90:10+0.1% of TFA). 60 mg of (Z) 1-[2-(5,6,7,8-tetrahydro-5,5,8,8-tetramethyl)naphthalenylmethylene]-1,2,3,4-tetrahydro-naphthalene-6-carboxylic acid, (CB80830) is obtained (yield=17%) and 100 mg of (E) 1-[2-(5,6,7,8-tetrahydro-5,5,8,8-tetramethyl)naphthalenylmethylene]- 1,2,3,4-tetrahydro-naphthalene-6-carboxylic acid, (CB66049) (yield=29%).

a) (Z) 1-]2-(5,6,7,8-tetrahydro-5,5,8,8-tetramethyl)-naphthalenylmethylene]-1,2,3,4-tetrahydro-naphthalene-6-carboxylic acid (CB80830) of formula:

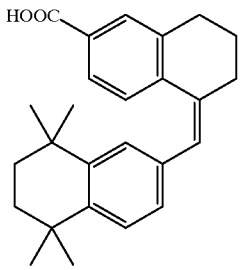

M.Pt. (° C.)=218–220.
IR (cm⁻¹): 3100; 2954; 1686; 1604; 1430; 1434. 1290.
NMR¹H 200 MHz (CDCl₃): 1.09 and 1.24 (2s, 12H, 5,5,8,8-Me); 1.62 (s, 4H, 6,7-Me); 1.68–2.15 (m, 2H); 2.51 (t, 2H, J 6.6 Hz); 2.91 (t, 2H, J 6.6 Hz); 6.49 (s, 1H); 6.93 (dd, 1H, J 1.3 Hz J 8 Hz); 7.10–7.16 (m, 2H); 7.34 (d, 1H, J 8 Hz); 7.53 (d, 1H, J 8 Hz); 7.84 (m, 1H).
MS EI, 70 eV (m/z, % intensity) 374 (100, M %); 359 (67).
MSHR EI 70 eV: M_tr=374.2249 for C₂₆H₃₀O₂ M_th=374.2246.

HPLC Column Waters HR C₁₈, 8×100 mm, 6 μ, detector UV Waters 486 to 260 nm, flow rate 3 ml/min, eluent MeOH:H₂O=90:10+0.1% TFA, acid (CB80830) tr=4.71 min. 96.9%.

b) (E) 1-[2-(5,6,7,8-tetrahydro-5,5,8,8-tetramethyl)-naphthalenylmethylene]-1,2,3,4-tetrahydronaphthalene-6-carboxylic acid (CB66049) of formula:

M.Pt. (° C.)=234.
IR (cm⁻¹) 3300; 2960; 1680; 1602.; 1430; 1294; 1186.
NMR¹H 200 MHz (CDCl₃): 1.28 and 1.29 (2s, 12H, 5,5,8,8-Me); 1.69 (s, 4H, 6,7-Me); 1.81–1.88 (m, 2H); 2.82–2.90 (m, 4H); 7.11 (s, 1H); 7.14–7.19 (m, 1H); 7.28–7.32 (m, 2H); 7.75 (d, 1H, J 8 Hz); 7.85–7.91 (m, 2H).
MS EI, 70 eV (m/z, % intensity): 374 (100, M %); 359 (67); 208 (35); 168 (39).
MSHR EI 70 eV: M_tr=374.2257 for C₂₆H₃₀O₂ M_th=374.2246.

HPLC Column Waters HR C₁₈, 8×100 mm, 6 μ, detector UV Waters 486 to 260 nm, flow rate 3 ml/min, eluent MeOH:H₂O=90:10+0.1% TFA, acid (CB66049) tr=6.26 min. 96.9%.

EXAMPLE 3

Preparation of (E) 5-[1-[2-(5,6,7,8-tetrahydro-5,5,8,8-tetramethyl)-2-naphthalenylmethylene]-1,2,3,4-tetrahydronaphthalenyl]-1H-tetrazole, (CB44858)

Dibutyl tin oxide (15 mg, 0.06 mmol) and trimethylsilyl azide (0.133 ml, 1 mmol) are added successively to a solution of (E) 6-cyano-1-2-(5,6,7,8-tetrahydro-5,5,8,8-tetramethyl)naphthalenylmethylene]-1,2,3,4-tetrahydronaphthalenyl]-1H-tetrazole (180 mg, 0.50 mmol) in anhydrous toluene (1 ml). The reaction medium is heated for 18 hours at reflux (110° C.) under an atmosphere of argon and with magnetic stirring. After returning to ambient temperature, the toluene is evaporated and the raw product purified by flash chromatography on silica (eluent MeOH:CH₂Cl₂=10:90) followed by precipitation in chloroform. 34.8 mg of a white powder 5-[1-[2-(5,6,7,8-tetrahydro-5,5,8,8-tetramethyl)naphthalenyl-methylene]-1,2,3,4-tetrahydronaphthalenyl]-1H-tetrazole (CB44858) is obtained (yield=17%) of formula:

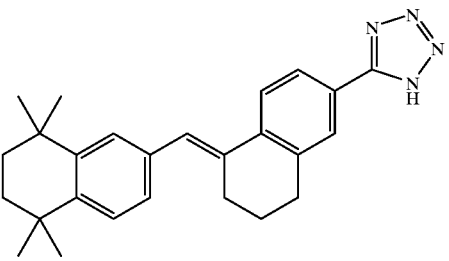

M.Pt. (° C.)=233–234.
IR (cm⁻¹): 3480; 2926; 1606; 1490; 1450.
NMR¹H 200 MHz (DMSO, D₆): 1.24 and 1.25 (2s, 12H, 5,5,8,8-Me); 1.64 (s, 4H, 6,7-CH₂); 1.74–1.80 (m, 2H); 2.77–2.89 (m, 4H); 7.16–7.21 (m, 2H); 7.30–7.35 (m, 2H); 7.82–7.86 (m, 2H); 7.97–8.00 (m, 1H).
MS IC, (isobutane) (m/z, % intensity): 399 (100, MH).
MSHR IC (isobutane): M_tr=399.2592 for C₂₆H₃₀N4 M_th=399.2549.

HPLC Column Waters HR C₁₈, 8×100 mm, 6 μ, detector UV Waters 486 to 260 nm, flow rate 3 ml/min, eluent MeOH H₂O=90:10+0.1% TFA, tetrazole (CB44858) tr=4.66 min. 98.0%.

EXAMPLE 4

Preparation of (Z) and (E) 1-[2-(5,6,7,8-tetrahydro-3,5,5,8,8-pentamethyl)naphthalenylmethylene]-1,2,3,4-tetrahydronaphthalene-6-carboxylic acids (CB53261 and CB95970)

1) (Z) and (E) 6-cyano-1-[2-(5,6,7,8-tetrahydro-3,5,5,8,8-pentamethyl)naphthalenylmethylene]-1,2,3,4-tetrahydronaphthalenes At −70° C. a molar solution of 1M tBuOK in THF (13.2 ml, 13.2 mmol) is added to a solution of (5,6,7,8-tetrahydro-3,5,5,8,8-pentamethyl-2-naphthalenyl)-6-methyl-triphenyl-phosphonium bromide (6.69 g, 12 mmol) in 17.3 ml of THF. Agitation is continued at −70° C. for 1 hour before adding 6-cyano-1-tetralone (1.03 g, 6.0 mmol) in 9 ml of THF at this temperature. The reaction medium is brought to ambient temperature and the reaction mixture is refluxed for 15 hours. After returning to ambient temperature, the reaction mixture is poured into 200 ml of a equivolume ice-water mixture. It is extracted with ether, dried over MgSO$_4$, filtered and the solvents evaporated. The raw product is purified by flash chromatography on silica (eluent:petroleum ether:diethyl ether=100:3). 0.91 g of the mixture of (Z) and (E) 6-cyano-1-[2-(5,6,7,8-tetrahydro-3,5,5,8,8-pentamethyl)naphthalenyl-methylene]-1,2,3,4-tetrahydro-naphthalenes (yield=41%) is obtained. ((Z):(E)=1:2).

a) (Z) 6-cyano-1-[2-(5,6,7,8-tetrahydro-3,5,5,8,8-pentamethyl)-naphthalenylmethylene]-1,2,3,4-tetrahydronaphthalene of formula:

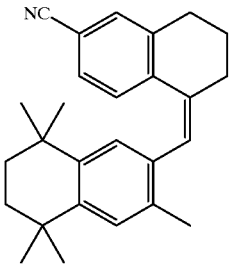

NMR$^1$H 200 MHz (CDCl$_3$): 0.97 and 1.25 (2s, 12H, 5,5,8,8-Me); 1.67 (s, 4H, 6,7-CH$_2$); 1.87–1.95 (m, 2H); 1.98 (s, 3H, ArMe); 2.52–2.58 (m, 2H); 2.62–2.69 (m, 2H); 6.53 (s, 1H, vinyl H); 7.00 (m, 2H, ArH); 7.45 (m, 1H, ArH); 7.70 (d, 2H, ArH, J 8 Hz).

b) (E) 6-cyano-1-[2-(5,6,7,8-tetrahydro-3,5,5,8,8-pentamethyl)-naphthalenylmethylene]-1,2,3,4-tetrahydronaphthalene of formula:

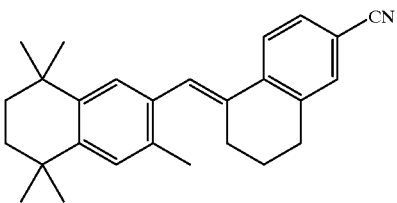

NMR$^1$H 200 MHz (CDCl$_3$): 1.26 and 1.28 (2s, 12H, 5,5,8,8-Me); 1.56 (s, 4H, 6,7-CH$_2$); 1.75–1.84 (m, 2H); 2.01 (s, 3H, ArMe); 2.82–2.92 (m, 2H); 6.86 (s, 1H, vinyl H); 7.01 (m, 1H, ArH); 7.06–7.14 (m, 2H, ArH); 7.37–7.39 (m, 2H, ArH).

2) (Z) and (E) 1-[2-(5,6,7,8-tetrahydro-3,5,5,8,8-pentamethyl)naphthalenylmethylene]-1,2,3,4-tetrahydronaphthalene-6-carboxylic acids (CB53261 and CB95970).

At ambient temperature, potassium hydroxide (1.81 g, 32.4 mmol) of potassium hydroxide is added to the mixture of (Z) and (E) 6-cyano-1-[2-(5,6,7,8-tetrahydro-3,5,5,8,8-pentamethyl)-naphthalenylmethylene]-1,2,3,4-tetrahydronaphthalenes (400 mg, 1.08 mmol) in solution in 3 ml of THF, 1.2 ml of water and 2 ml of ethanol. The reaction mixture is brought to reflux under magnetic stirring for 12 hours. After returning to ambient temperature the mixture is evaporated, taken up again in water (10 ml), acidified with 3N HCl, extracted with diethyl ether (3×50 ml), the ether phase dried over MgSO$_4$, filtered and evaporated. The raw product is purified by preparative HPLC (eluent:MeOH:H$_2$O=90:10+0.1% of TFA). 87.6 mg of (Z) 1-[2-(5,6,7,8-tetrahydro-3,5,5,8,8-pentamethyl) naphthalenylmethylene]-1,2,3,4-tetrahydro-naphthalene-6-carboxylic acid, (CB53261) is obtained (yield=21%) and 100 mg of (E) 1-(2-(5,6,7,8-tetrahydro-3,5,5,8,8-pentamethyl)-naphthalenylmethylene]-1,2,3,4-tetrahydronaphthalene-6-carboxylic acid, (CB95970) (yield=30%).

a) (Z) 1-[2-(5,6,7,8-tetrahydro-3,5,5,8,8-pentamethyl) naphthalenylmethylene]-1,2,3,4-tetrahydro-naphthalene-6-carboxylic acid, (CB53261) of formula:

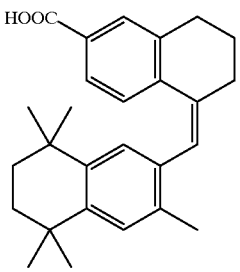

M.Pt. (° C.)=207.
IR (cm$^{-1}$): 2950; 1680; 1602; 1560; 1428; 1302.
NMR$^1$H 200 MHz (CDCl$_3$): 0.98 and 1.25 (2s, 12H, 5,5,8,8-Me); 1.59 (s, 4H, 6,7-CH$_2$); 1.99–2.05 (m, 2H); 2.18 (s, 3H, ArH); 2.57 (t, 2H, J 6 Hz); 2.93 (t, 2H, J 6 Hz); 6.51 (s, 1H); 6.92 (s, 1H); 7.00–7.05 (m, 2H); 7.43 (d, 1H, J 8 Hz); 7.81 (s, 1H).
MS EI, 70 eV (m/z, % intensity): 388 (100, M$^+$); 373 (78).
MSHR EI 70 eV: M$_{tr}$=388.2416 for C$_{27}$H$_{32}$O$_2$ M$_{th}$= 388.2402.
HPLC Column Waters HR C$_{18}$, 8×100 mm, 6 µ, detector UV Waters 486 to 260 nm, flow rate 3 ml/min, eluent MeOH:H$_2$O=90:10+0.1% TFA, acid (CB53261) tr=5.51 min. 97.5%.

b) (E.) 1-[2-(5,6,7,8-tetrahydro-3,5,5,8,8-pentamethyl) naphthalenylmethylene]-1,2,3,4-tetrahydro-naphthalene-6-carboxylic acid, (CB95970) of formula:

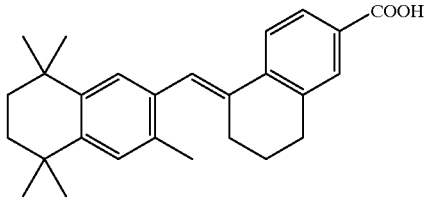

M.Pt. (° C.)=226–229.
IR (cm$^{-1}$): 3300; 2954; 1690; 1600; 1566; 1490; 1430; 1302; 1186.
NMR$^1$H 200 MHz (CDCl$_3$): 1.31 and 1.33 (2s, 12H, 5,5,8,8-Me); 1.72 (s, 4H, 6,7-CH$_2$); 1.85–1.91 (m, 2H); 2.30

(s, 3H, ArMe); 2.73 (t, 2H, J 6 Hz); 2.95 (t, 2H, J 6 Hz); 7.17 (s, 2H); 7.21 (s, 1H); 7.80 (d, 1H, ArH J 8 Hz); 7.93–7.97 (m, 2H, ArH).

MS EI, 70 eV (m/z, % intensity): 389 (35); 388 (100, M⁺); 373 (78).

MSHR EI 70 eV: $M_{tr}$=388.2400 for $C_{27}H_{32}O_2$ $M_{th}$= 388.2402.

HPLC Column Waters HR $C_{18}$, 8×100 mm, 6 μ, detector UV Waters 486 to 260 nm, flow-rate 3 ml/min, eluent MeOH:H₂O=90:10+0.1% TFA, acid (CB95970) tr=6.45 min. 98.7%.

EXAMPLE 5

Preparation of (Z) and (E) 5-[1-[2-(5,6,7,8-tetrahydro-3,5,5,8,8-pentamethyl)naphthalenyl-methylene]-1,2,3,4-tetrahydronaphthalenyl]-1H-tetrazoles (CB02305 and CB58248)

Dibutyl tin oxide (39 mg, 0.16 mmol) and trimethylsilyl azide (0.350 ml, 2.64 mmol) are added successively to a solution of (Z) and (E) 6-cyano-1-[2-(5,6,7,8-tetrahydro-3, 5,5,8,8-pentamethyl)naphthalenyl-methylene]-1,2,3,4-tetrahydro-naphthalenes (Z/E=1/2) (490 mg, 1.32 mmol) in anhydrous toluene (2.6 ml). The reaction medium is heated for 15 hours at reflux (110° C.) under an atmosphere of argon and with magnetic stirring. After returning to ambient temperature, the toluene is evaporated and the raw product purified by HPLC preparative chromatography (eluent MeOH:H₂O=88:12+0.1% TFA). 96 mg of a solid (Z) 5-[1-[2-(5,6,7,8-tetrahydro-3,5,5,8,8-pentamethyl)naphthalenyl-methylene]-1,2,3,4-tetrahydronaphthalenyl]-1H-tetrazole (CB02305) is obtained (yield=18%) and 187 mg of a solid (E) 5-[1-[2-(5,6,7,8-tetrahydro-3,5,5,8,8-pentamethyl)naphthalenyl-methylene]-1,2,3,4-tetrahydronaphthalenyl]-1H-tetrazole (CB58248)(yield=34%)

1) (Z) 5-[1-[2-(5,6,7,8-tetrahydro-3,5,5,8,8-pentamethyl)naphthalenyl-methylene]-1,2,3,4-tetrahydro-naphthalenyl]-1H-tetrazole (CB02305) of formula:

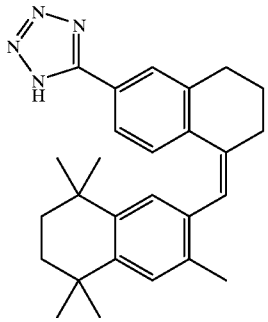

M.Pt. (° C.)=148.

IR (cm⁻¹): 2994; 1686; 1600; 1458; 1264.

NMR¹H 200 MHz (CDCl₃): 0.94 and 1.22 (2s, 12H, 5,5,8,8-Me); 1.54 (m, 4H, 6,7-CH₂); 1.67–2.03 (m, 2H); 2.18 (s, 3H, ArMe); 2.53–2.59 (m, 2H); 2.89–2.95 (m, 2H); 6.50 (s, 1H); 6.94 (s, 1H); 7.09 (s, 1H); 7.13–7.17 (m, 2H); 7.42 (d, 1H, J 8.7 Hz).

MS EI, 70 eV (m/z, % intensity): 412 (100, M⁺); 384 (83).

MSHR EI 70 eV: $M_{tr}$=412.2637 for $C_{27}H_{32}N_4$ $M_{th}$= 412.2627.

HPLC Column Waters HR $C_{18, 8\times100}$ mm, 6 μ, detector UV Waters 486 to 260 nm, flow rate 3 ml/min, eluent MeOH:H₂O=90:10+0.1% TFA, tetrazole (CB02305) tr=5.44 min. 99.4%.

2) (E) 5-[1-[2-(5,6,7,8-tetrahydro-3,5,5,8,8-pentamethyl)naphthalenyl-methylene]-1,2,3,4-tetrahydro-naphthalenyl]-1H-tetrazole (CB58248) of formula:

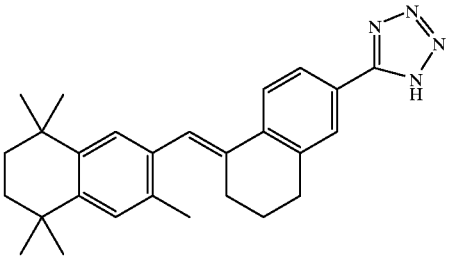

M.Pt. (° C.)=237–239.

IR (cm⁻¹): 3400; 2922; 1612; 1566; 1494; 1450; 1392; 1362.

NMR¹H 200 MHz (DMSO D₆): 1.07 (2s, 12H, 5,5,8,8-Me); 1.22 (m, 4H, 6,7-CH₂); 1.73–1.75 (m, 2H); 2.20 (s, 3H, ArMe); 2.59–2.69 (m, 2H); 2.87–2.93 (m, 2H); 7.12–7.17 (m, 3H); 7.82–7.85 (m, 2H); 7.99 (d, 1H, J 8.7 Hz).

MS EI, 70 eV (m/z, % intensity): 412 (100, M⁺); 384 (86); 369 (23).

MSHR EI 70 eV: $M_{tr}$=412.2627 for $C_{27}H_{32}N_4$ $M_{th}$= 412.2627.

HPLC Column Waters HR $C_{18}$, 8×100 mm, 6 μ, detector UV Waters 486 to 260 nm, flow rate 3 ml/min, eluent MeOH:H₂O=90:10+0.1% TFA, tetrazole (CB02305) tr=6.31 min. 99.4%.

a) 2-methyl-5-bromo-1-indanone.

A solution of 5-bromo-1-indanone (3.75 g, 17.76 mmol) in 18 ml of anhydrous THF is brought to −20° C. under an atmosphere of argon and with magnetic stirring. A 1M solution of t-BuOK in THF (18 ml, 18 mmol) is added with a syringe and the stirring continued for 3 hours at ambient temperature. At 0° C., 10 ml of distilled water is added and the mixture then extracted with ether (4×75 ml), dried over MgSO₄, filtered and evaporated to obtain a raw product that is incorporated onto silica and purified by flash chromatography on silica (eluent ether:petroleum ether=2:98 up to 5:95). In order of elution, one obtains 1.85 g of a yellowish oil, 2,2-dimethyl-5-bromo-1-indanone (yield=43%), 0.50 g of a white solid 2-methyl-5-bromo-1-indanone (yield=13%) and 1.20 g of a white solid (32%) the starting material, 5-bromo-1-indanone.

NMR¹H 200 MHz (CDCl₃): 1.25 (d, 3H, Me J 7 Hz); 2.55–2.75 (m, 2H, —CH₂—); 3.25–3.45 (m, 1H, —CHMe—); 7.40–7.65 (m, 3H, ArH).

b) (E) and (Z) 1-[2-(5,6,7,8-tetrahydro-5,5,8,8-tetramethyl(naphthalenylmethylene]2,3-dihydro-2-methyl-5-bromo-1H-indenes.

At −70° C. a molar solution of tBuOK in THF (8.44 ml, 8.44 mmol) is added to a solution of (5,6,7,8-tetrahydro-5, 5,8,8-tetramethyl-2-naphthalenyl)-6-methyl-triphenyl-phosphonium bromide (4.21 g, 8.44 mmol) in 15 ml of anhydrous THF. Agitation is continued at −70° C. for 1 hour before adding a solution of 2-methyl-5-bromo-1-indanone (0.95 g, 4.22-mmol) in 5 ml of anhydrous THF. The reaction medium is brought to ambient temperature and is stirred for 16 hours. The reaction mixture is then poured into 150 ml of an ice-water mixture and then extracted with ether, dried over MgSO₄, filtered and evaporated. The raw product is purified by flash chromatography on silica (eluent:pure petroleum ether). 1.56 g of a yellowish oil is obtained, the mixture of (Z) and (E) 1-[21-(5,6,7,8-tetrahydro-5,5,8,8-tetramethyl(naphthalenyl-methylene]2,3-dihydro-2-methyl- 5-bromo-1H-indene (yield=90%) in proportion E:Z=75:25 as determined by NMR¹H 200 MHz and having the following formula:

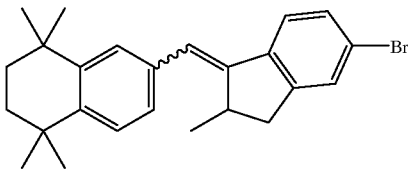

NMR¹H 200 MHz (CDCl₃): 1.15–1.40 (m, 15H, 5,5,8,8-Me and Me); 1.70 (s, 4H, 6,7-CH₂); 2.50–2.70 (m, 1H, —CH₂— indene); 3.05–3.35 (m, 1.25H, 0.75 H —CH₂— indene isomer E and 0.25 H —CH₂— indene isomer Z and 0.25H —CHMe— indene isomer Z); 3.55–3.75 (m, 0.75H, —CHMe— indene isomer E); 6.47 (d, 0.25H, vinyl H isomer Z); 6.83 (d, 0.75H, vinyl H isomer E J 1.5 Hz); 6.95–7.50 (m, 6H, ArH).

c) (E) and (Z) 1-[2-(5,6,7,8-tetrahydro-5,5,8,8-tetramethyl(naphthalenylmethylene]-2,3-dihydro-2-methyl-5-cyano-1H-indenes.

At ambient temperature, copper cyanide (0.51 g, 5.71 mmol) is added to a solution of (E) and (Z) 1-[2-(5,6,7,8-tetrahydro-5,5,8,8-tetramethyl(naphthalenyl-methylene]-2,3-dihydro-2-methyl-5-bromo-1H-indene (1.56 g, 3.81 mmol) in 15 ml of anhydrous DMF. The reaction medium is brought to reflux for 24 hours under an atmosphere of argon. After returning to ambient temperature, the reaction mixture is diluted with ether (100 ml) and filtered on celite. The organic phase is washed with a saturated aqueous solution of NaHCO₃ (3×25 ml) and then dried over MgSO₄, filtered and evaporated. The raw product is purified by flash chromatography on silica (eluent petroleum ether:ether=98:2). 0.21 g of a yellowish oil (Z) 1-[2-(5,6,7,8-tetrahydro-5,5,8,8-tetramethyl(naphthalenylmethylene]-2,3-dihydro-2-methyl-5-cyano-1H-indene is obtained (yield=15.5%) and then 0.60 g of a yellowish solid (recrystallizable in hexane) (E) 1-[2-(5,6,7,8-tetrahydro-5,5,8,8-tetramethyl (naphthalenylmethylene]-2,3-dihydro-2-methyl-5-cyano-1H-indene (yield=44%).

Isomer (Z):

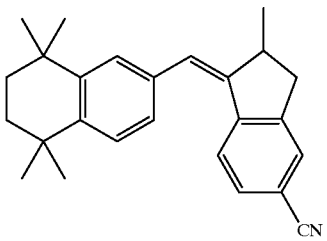

NMR¹H 200 MHz (CDCl₃): 1.23 and 1.30 (2s, 12H, 5,5,8,8-Me); 1.28 (d, 3H, Me indene J 7 Hz); 1.70 (s, 4H, 6,7-CH₂); 2.62 (m, 1H, —CH₂— indene); 3.14 (m, 1H, —CH₂— indene); 3.21 (t, 1H, —CHMe— indene J 7 Hz); 6.61 (s, 1H, vinyl H); 7.06 (dd, 1H, ArH J 1.1 Hz and J 8 Hz); 7.15–7.55 (m, 5H, ArH).

Isomer (E):

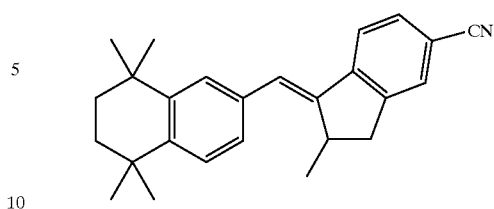

M. Pt. (° C.)=104.
NMR¹H 200 MHz (CDCl₃): 1.22 (d, 3H, Me indene J 7 Hz); 1.29 (s, 6H, 2 Me); 1.31 (s, 3H, Me); 1.33 (s, 1H, Me); 1.70 (s, 4H, 6,7-CH₂); 2.67 (d, 1H, —CH₂— indene J 16.5 Hz); 3.27 (dd, 1H, —CH₂— indene J 16.5 Hz and J 7.8 Hz); 3.68 (q, 1H, —CHMe— indene J 16.5 Hz J 7.8 Hz); 6.94 (d, 1H, vinyl H J 1.4 Hz); 7.25–7.65 (m, 6H, ArH).

d) (E) 1-[2-(5,6,7,8-tetrahydro-5,5,8,8-tetramethyl)-naphthalenylmethylene]-2,3-dihydro-2-methyl-1H-indene-5-carboxylic acid (CB52809)

Potassium hydroxide (0,64 g, 11.2 mmol) is added to a suspension of (E) 1-[2-(5,6,7,8-tetrahydro-5,5,8,8-tetramethyl(naphthalenylmethylene]-2,3-dihydro-2-methyl-5-cyano-1H-indene (0.20 g, 0.56 mmol) in a hydroethanolic solution (H₂O 0.80 ml and EtOH 5.0 ml) and 1 ml of THF. The mixture is refluxed with magnetic stirring for 48 hours. It is then taken up in water (20 ml) acidified with 1N HCl, extracted with ether (3×50 ml), dried by MgSO₄, filtered and evaporated. After washing with pentane, filtration and drying 0.19 g of a white powder is obtained (E) 1-[2-(5,6,7,8-tetrahydro-5,5,8,8-tetramethyl)naphthalenyl-methylene]-2,3-dihydro-2-methyl-1H-indene-5-carboxylic acid (CB52809) (yield=91%.) of formula:

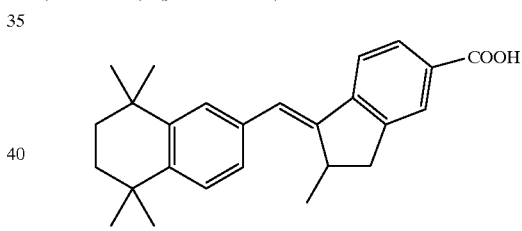

M.Pt. (° C.)=206.
NMR¹H 200 MHz (CDCl₃): 1.21 (d, 3H, Me indene J 6.9 Hz); 1.29 (s, 6H, 2 Me); 1.31 (s, 3H, Me); 1.32 (s, 3H, Me); 1.70 (s, 4H, 6,7-CH₂); 2.70 (d, 1H, —CH₂— indene J 16.4 Hz); 3.30 (dd, 1H, —CH₂— indene J 16.4 Hz and J 7.5 Hz); 3.69 (m, 1H, —CHMe— indene); 6.96 (s, 1H, vinyl H); 7.31 (s, 2H ArH); 7.48 (s, 1H, ArH); 7.63 (d, 1H, ArH J 8.4 Hz); 7.99 (d, 1H, ArH J 8.4 Hz); 8.01 (s, 1H, ArH).

MS EI, 70 eV (m/z, % intensity): 374 (M 100%); 359 (M—CH₃, 95), 143 (21).

MSHR EI 70 eV: $M_{tr}$=374.2238 for $C_{22}H_{30}O_2$ $M_{th}$=354.2446.

HPLC Column Waters HR $C_{18}$, 8×100 mm, 6 μ, detector UV Waters 486 to 260 nm, flow rate 3 ml/min, eluent MeOH:H₂O=90:10+0.1% TFA, acid (CB52809) tr=6.21 min. 97.5%; impurity tr=7.37 min 1.4%.

e) (Z) 1-[2-(5,6,7,8-tetrahydro-5,5,8,8-tetramethyl)-naphthalenylmethylene]-2,3-dihydro-2-methyl-1H-indene-5-carboxylic acid (CB91261) and (Z) 1-[2-(5,6,7,8-tetrahydro-5,5,8,8-tetramethyl)naphthalenyl-methylene]-2,3-dihydro-2-methyl-1H-indene-5-amide (CB96711).

Potassium hydroxide (0,64 g, 11.2 mmol) is added to a suspension of (Z) 1-[2-(5,6,7,8-tetrahydro-5,5,8,8- tetramethyl(naphthalenylmethylene]-2,3-dihydro-2-methyl-5-cyano-1H-indene (0.20 g, 0.56 mmol) in a hydroethanolic solution (H₂O 0.80 ml and EtOH 5.0 ml) and 1 ml of THF. The mixture is refluxed with magnetic stirring for 48 hours. It is then taken up in water (20 ml) acidified with 1N HCl, extracted with ether (3×50 ml), dried by MgSO₄, filtered and evaporated. The raw product is purified by preparative HPLC on a Waters column HR C$_{18}$ (25×100 mm) with MeOH:H₂O=90:10+0.1% TFA as eluent. 0.04 g of a white solid is obtained (Z) 1-[2-(5,6,7,8-tetrahydro-5,5,8,8-tetramethyl)naphthalenyl-methylene]-2,3-dihydro-2-methyl-1H-indene-5-amide (CB96711) (yield=19%) and 0.12 g of a white solid (Z) 1-[2-(5,6,7,8-tetrahydro-5,5,8,8-tetramethyl)-naphthalenylmethylene]-2,3-dihydro-2-methyl-1H-indene-5-carboxylic acid (CB91261) (yield=57%).

(Z) 1-[2-(5,6,7,8-tetrahydro-5,5,8,8-tetramethyl) naphthalenyl-methylene]-2,3-dihydro-2-methyl-1H-indene-5-amide (CB96711):

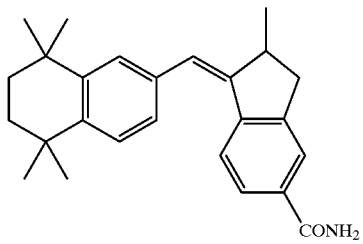

M. Pt. (° C.)=187–188.

NMR$^1$H 200 MHz (CDCl₃): 1.22 and 1.29 (2s, 12H, 5,5,8,8-Me); 1.27 (d, 3H, Me indene J 7 Hz); 1.70 (s, 4H, 6,7-CH₂); 2.61 (m, 1H, —CH₂— indene); 3.00–3.30 (m, 2H, —CH₂— and —CHMe— indene); 6.54 (s, 1H, vinyl H); 7.08 (dd, 1H, ArH J 1.7 Hz and J 8.1 Hz); 7.23–7.45 (m, 4H, ArH); 7.67 (s, 1H, ArH).

MS EI 70 eV (m/z, % intensity): 373 (M, 100%); 358 (M⁺—CH₃, 60), 185 (12); 141 (11); 129 (12); 128 (25).

MSHR EI 70 eV: M$_{tr}$=373.2406 for C$_{26}$H$_{31}$NO M$_{th}$=373.2406.

HPLC: Column Waters HR C$_{18}$, 8×100 mm, 6 μ, detector UV Waters 486 to 260 nm, flow rate 3 ml/min, eluent MeOH:H₂O=90:10+0.1% TFA, amide (CB96711) tr=3.57 min. 99.5%; impurity tr=18.4 min 0.25%.

(Z) 1-[2-(5,6,7,8-tetrahydro-5,5,8,8-tetramethyl)-naphthalenylmethylene]-2,3-dihydro-2-methyl-1H-indene-5-carboxylic acid (CB91261) of formula:

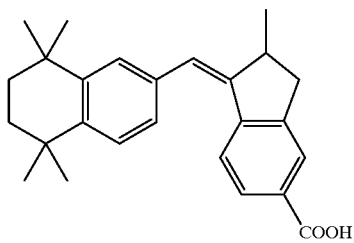

M. Pt. (° C.)=196–197.

NMR$^1$H 200 MHz (CDCl₃): 1.22 and 1.29 (2s, 12H, 5,5,8,8-Me); 1.27 (d, 3H, Me indene J 7 Hz); 1.70 (s, 4H, 6,7-CH₂); 2.63 (m, 1H, —CH₂— indene); 3.03–3.30 (m, 2H, —CH₂— and —CHMe— indene); 6.57 (s, 1H, vinyl H); 7.07 (dd, 1H, ArH J 1.7 Hz and J 8.1 Hz); 7.25–7.45 (m, 3H, ArH); 7.67 (dd, 1H, ArH J 1.7 Hz and J 8.1 Hz); 7.97 (s, 1H, ArH).

MS EI 70 eV (m/z, % intensity): 374 (M, 100%); 359 (M⁺—CH₃, 60), 143 (29); 128 (25).

MSHR EI 70 eV: M$_{tr}$=374.2238 for C$_{26}$H$_{30}$O$_2$ M$_{th}$=374.2246.

HPLC: Column Waters HR C$_{18}$, 8×100 mm, 6 μ, detector UV Waters 486 to 260 nm, flow rate 3 ml/min, eluent MeOH:H₂O=90:10+0.1% TFA, acid (CB91261) tr=6.17 min. 97.9%; impurity tr=7.4 min 1.2%.

f) (E) 5-[1-[2-(5,6,7,8-tetrahydro-5,5,8,8-tetramethyl) naphthalenylmethylene]-2,3-dihydro-2-methyl-1H-indenyl]-1H-tetrazole (CB69831).

Dibutyl tin oxide (30 mg) and trimethylsilyl azide (0.31 ml, 2.36 mmol) are added successively to a solution of (E) 1-[2-(5,6,7,8-tetrahydro- 5,5,8,8-tetramethyl-(naphthalenylmethylene]-2,3-dihydro-2-methyl-5-cyano-1H-indene (0.42 g, 1.18 mmol) in anhydrous toluene (2.50 ml). The reaction medium is heated for 16 hours at reflux (110° C.) under an atmosphere of argon and with magnetic stirring. After cooling, the toluene is evaporated, the product taken up in dichloromethane and incorporated onto silica. It is purified by flash chromatography on silica (eluent CH₂Cl₂ then MeOH:CH₂Cl₂=5:95). After evaporation, washing with pentane, filtration and then drying at the pump, 0.10 g of an off-white powder is obtained (E) 5-[1-[2-(5,6,7,8-tetrahydro-5,5,8,8-tetramethyl)naphthalenylmethylene]-2,3-dihydro-2-methyl-1H-indenyl]-1H-tetrazole (CB69831) (yield=21%) with the following formula:

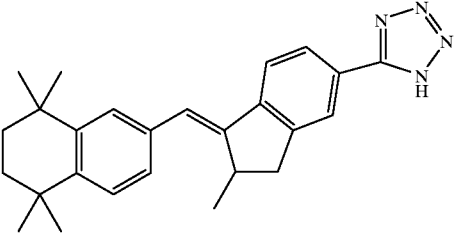

M. Pt. (° C.)=149.

NMR$^1$H 200 MHz (CDCl₃): 1.22 (d, 3H, Me, J 6.9 Hz); 1.28 (s, 6H, 2 Me); 1.29 (s, 3H, Me); 1.30 (s, 3H, Me); 1.59 (s, 4H, 6,7-CH₂); 2.69 (d, 1H, —CH₂— indene J 16.4 Hz); 3.29 (dd, 1H, —CH₂— indene J 7.5 Hz J 16.4 Hz); 3.70 (m, 1H, —CHMe— indene); 6.92 (d, 1H, vinyl H J 1.3 Hz); 7.29 (s, 1H, ArH); 7.46 (s, 1H, ArH); 7.69 (d, 1H, ArH J 8.0 Hz); 7.94 (d, 1H, ArH J 8.0 Hz); 7.99 (s, 1H, ArH).

MS EI 70 eV (m/z, % intensity): 398 (M, 62%); 370 (100), 355 (39); 185 (12); 143 (14).

MSHR EI 70 eV: M$_{tr}$=398.2466 for C$_{26}$H$_{30}$N$_4$ M$_{th}$=373.2470.

HPLC: Column Waters HR C$_{18}$, 8×100 mm, 6 μ, detector UV Waters 486 to 260 nm, flow rate 3 ml/min, eluent MeOH:H₂O=90:10+0.1% TFA, tetrazole (CB69831) tr=4.32 min. 98.6%; impurity tr=5.77 min 0.30%.

EXAMPLE 6

Preparation of (E) and (Z) 1-[2-(5,6,7,8-tetrahydro-5,5,8,8-tetramethyl)naphthalenylmethylene]-2,3-dihydro-1H-indene-5-carboxylic acids, (CB78937 and CB27871) and (E) and (Z) 5-[1-[2-(5,6,7,8-tetrahydro-5,5,8,8-tetramethyl) naphthalenylmethylene]-2,3-dihydro-1H-indenyl]-1H-tetrazoles, (CB99811 and CB94083).

a) (E) and (Z) 1-[2-(5,6,7,8-tetrahydro-5,5,8,8-tetramethyl)naphthalenylmethylene]-2,3-dihydro-5-bromo-1H-indenes.

At −70° C. a 1M solution of t-BuOK in THF (12.56 ml, 12.56-mmol) is added to a solution of (5,6,7,8-tetrahydro-5,5,8,8-tetramethyl-2-naphthalenyl)-6-methyl-triphenyl-phosphonium bromide (7.00 g, 12.56 mmol) in 20 ml of anhydrous THF under an argon atmosphere and with magnetic agitation. Agitation is continued at −70° C. for 1 hour before adding a solution of 5-bromo-1-indanone (1.33 g, 6.28 mmol) in 15 ml of anhydrous THF. The reaction medium is brought to ambient temperature and is stirred for 16 hours. The reaction mixture is then poured into 150 ml of an ice-water mixture and then extracted with ether (4×100 ml), dried over MgSO$_4$, filtered and evaporated. The raw product is purified by flash chromatography on silica (eluent:pure petroleum ether). 0.57 g of a colorless oil is obtained (Z) 1-[2-(5,6,7,8-tetrahydro-5,5,8,8-tetramethyl) naphthalenylmethylene]-2,3-dihydro-5-bromo-1H-indene (yield=23%) and then 1.42 g of a yellowish solid (E) 1-[2-(5,6,7,8-tetrahydro- 5,5,8,8-tetramethyl) naphthalenylmethylene]-2,3-dihydro-5-bromo-1H-indene (yield 57%).

Isomer (Z):

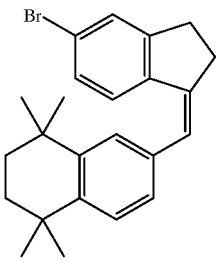

NMR$^1$H 200 MHz (CDCl$_3$): 1.23 and 1.29 (2s, 12H, 5,5,8,8-Me); 1.69 (s, 4H, 6,7-CH$_2$); 2.80–3.00 (m, 4H, —CH$_2$— indene); 6.56 (s, 1H, vinyl H); 7.00–7.10 (m, 2H, ArH); 7.15–7.40 (m, 4H, ArH).

Isomer (E):

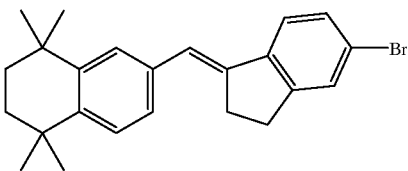

M.Pt. (° C.)=141–142.
NMR$^1$H 200 MHz (CDCl$_3$): 1.28 and 1.30 (2s, 12H, 5,5,8,8-Me); 1.69 (s, 4H, 6,7-CH$_2$); 3.07 (s broad, 4H, —CH$_2$— indene); 6.88 (s, 1H, vinyl H); 7.15–7.50 (m, 6H, ArH).

MS EI 70 eV (m/z, % intensity): 396–394 (M$^+$, 99%–98%); 381–379 (100–99).

b) (E) 1-[2-(5,6,7,8-tetrahydro-5,5,8,8-tetramethyl) naphthalenylmethylene]-2,3-dihydro-5-cyano-1H-indene.

At ambient temperature, copper cyanide (0.35 g, 3.94 mmol) is added to a solution of (E) 1-[2-(5,6,7,8-tetrahydro-5,5,8,8-tetramethyl(naphthalenyl-methylene]-2,3-dihydro-5-bromo-1H-indene (1.20 g, 3.03 mmol) in 10 ml of anhydrous DMF. The reaction medium is brought to reflux for 70 hours under an atmosphere of argon. After returning to ambient temperature, the reaction mixture is diluted with ether (100 ml) and filtered on celite. The organic phase is washed with a saturated aqueous solution of NaHCO$_3$ (3×25 ml) and then dried over MgSO$_4$, filtered and evaporated. The raw product is purified by flash chromatography on silica (eluent petroleum ether:ether=98:2). 0.45 g of a white solid (E) 1-[2-(5,6,7,8-tetrahydro-5,5,8,8-tetramethyl (naphthalenylmethylene]-2,3-dihydro-5-cyano-1H-indene is obtained (yield=43%)

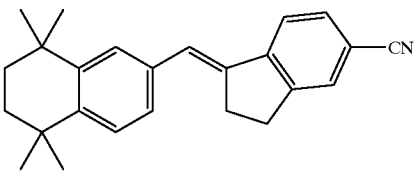

M.Pt. (° C.)=160–161.
NMR$^1$H 200 MHz (CDCl$_3$): 1.29 and 1.31 (2s, 12H, 5,5,8,8-Me); 1.69 (s, 4H, 6,7-CH$_2$); 3.11 (s broad, 4H, —CH$_2$— indene); 7.01 (s, 1H, vinyl H); 7.23–7.55 (m, 5H, ArH); 7.62 (d, 1H, ArH J 8 Hz).

MS EI 70 eV (m/z, % intensity): 341 (M$^+$, 67%); 326 (100).

c) (E) 1-[2-(5,6,7,8-tetrahydro-5,5,8,8-tetramethyl)-naphthalenylmethylene]-2,3-dihydro-1H-indene-5-carboxylic acid, (CB78937).

Potassium hydroxide (0,41 g, 7.30 mmol) is added to a suspension of (E) 1-[2-(5,6,7,8-tetrahydro-5,5,8,8-tetramethyl(naphthalenylmethylene]-2,3-dihydro-5-cyano-1H-indene (0.25 g, 0.73 mmol) in a hydroethanolic solution (H$_2$O 0.50 ml and EtOH 4.5 ml. The mixture is refluxed with magnetic stirring for 7 hours. After cooling the reaction mixture, it is then taken up in distilled water (20 ml), acidified with 1N HCl (15 ml), extracted with ether (3×40 ml), dried by MgSO$_4$, filtered and evaporated. After washing with hexane, filtration and drying, one obtains 0.20 g of a white solid (E) 1-[2-(5,6,7,8-tetrahydro-5,5,8,8-tetramethyl)-naphthalenylmethylene]-2,3-dihydro-1H-indene-5-carboxylic acid, (CB78937) (yield=76%)

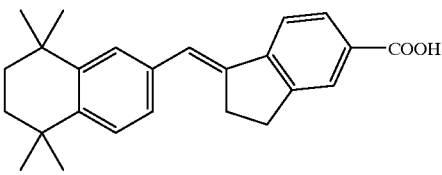

M.Pt. (° C.)=294.
NMR$^1$H 200 MHz (CDCl$_3$): 1.29 and 1.32 (2s, 12H, 5,5,8,8-Me); 1.70 (s, 4H, 6,7-CH$_2$); 3.14 (s, 4H, —CH$_2$— indene); 7.05 (s, 1H, vinyl H); 7.25–7.35 (m, 2H, ArH); 7.42 (s, 1H, ArH); 7.65 (d, 1H, ArH J 8 Hz); 7.98 (d, 1H, ArH J 8.1 Hz); 8.01 (s, 1H, ArH).

MS EI 70 eV (m/z, % intensity): 360 (M$^+$, 72%); 345 (M$^+$—CH$_3$, 100), 143 (22); 129 (55).

MSHR EI 70 eV: M$_{tr}$=360.2103 for C$_{25}$H$_{28}$O$_2$ M$_{th}$=360.2090.

HPLC: Column Waters HR C$_{18}$, 8×100 mm, 6 μ, detector UV Waters 486 to 260 nm, flow rate 3 ml/min, eluent MeOH:H$_2$O=90:10+0.1% TFA, acid (CB78937) tr=4.31 min. 99.8%.

d) (E) 5-[1-[2-(5,6,7,8-tetrahydro-5,5,8,8-tetramethyl) naphthalenylmethylene]-2,3,-dihydro-1H-indenyl]-1H-tetrazole (CB99811).

Dibutyl tin oxide (10 mg) and trimethylsilyl azide (0.16 ml, 1.22 mmol) are added successively to a solution of (E)

1-[2-(5,6,7,8-tetrahydro-5,5,8,8-tetramethyl-(naphthalenylmethylene]-2,3-dihydro-5-cyano-1H-indene (0.20 g, 0.59 mmol) in anhydrous toluene (1.25 ml). The reaction medium is heated for 16 hours at reflux (110° C.) under an atmosphere of argon and with magnetic stirring. After cooling, the toluene is evaporated, the product taken up in dichloromethane and incorporated onto silica. It is purified by flash chromatography on silica (eluent $CH_2Cl_2$ then MeOH:$CH_2Cl_2$=5:95). After evaporation, and then drying at the pump, 0.14 g of a white solid is obtained (E) 5-[1-[2-(5,6,7,8-tetrahydro-5,5,8,8-tetramethyl)naphthalenylmethylene]-2,3,-dihydro-1H-indenyl]-1H-tetrazole (CB99811) (yield=60%) of formula:

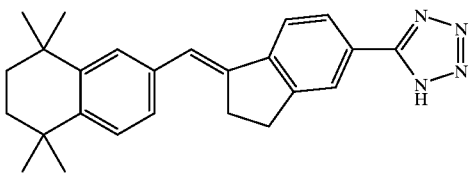

M. Pt. (° C.)=248.

NMR$^1$H 200 MHz (CDCl$_3$): 1.28 and 1.32 (2s, 12H, 5,5,8,8-Me); 1.71 (s, 4H, 6,7-CH$_2$); 3.19 (s, 4H, —CH$_2$—indene); 7.16 (s, 1H, vinyl H); 7.25–7.40 (m, 2H, ArH); 7.52 (s, 1H, ArH); 7.84 (d, 1H, ArH J 8.1 Hz); 8.00 (d, 1H, ArH J 8.1 Hz); 8.04 (s, 1H, ArH).

MS EI 70 eV (m/z, % intensity): 384 (M$^+$, 24%); 356 (62), 341 (32); 61 (100).

MSHR EI 70 eV: M$_{tr}$=384.2291 for C$_{25}$H$_{28}$N$_4$ M$_{th}$=384.2314.

HPLC: Column Waters HR C$_{18}$, 8×100 mm, 6 μ, detector UV Waters 486 to 260 nm, flow rate 3 ml/min, eluent MeOH:H$_2$O=90:10+0.1% TFA, tetrazole (CB99811) tr=4.37 min. 95.2%.

e) (Z) 1-[2-(5,6,7,8-tetrahydro-5,5,8,8-tetramethyl-(naphthalenylmethylene]-2,3-dihydro-5-cyano-1H-indene.

At ambient temperature, copper cyanide (0.16 g, 1.81 mmol) is added to a solution of (Z) 1-[2-(5,6,7,8-tetrahydro-5,5,8,8-tetramethyl (naphthalenyl-methylene]- 2,3-dihydro-5-bromo-1H-indene (0.51 g, 1.29 mmol) in 5 ml of anhydrous DMF. The reaction medium is brought to reflux for 30 hours under an atmosphere of argon. After returning to ambient temperature, the reaction mixture is diluted with ether (100 ml) and filtered on celite. The organic phase is washed with a saturated aqueous solution of NaHCO$_3$ (3×25 ml) and then dried over MgSO$_4$, filtered and evaporated. The raw product is purified by flash chromatography on silica (eluent petroleum ether:ether=98:2). 0.16 g of a white solid (Z) 1-[2-(5,6,7,8-tetrahydro-5,5,8,8-tetramethyl (naphthalenylmethylene]-2,3-dihydro-5-cyano-1H-indene is obtained (yield=36%) of formula:

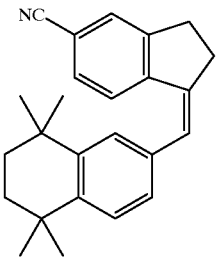

M.Pt. (° C.)=132–135.

NMR$^1$H 200 MHz (CDCl$_3$): 1.22 and 1.29 (2s, 12H, 5,5,8,8-Me); 1.69 (s, 4H, 6,7-CH$_2$); 2.80–3.10 (m, 4H, —CH$_2$— indene); 6.70 (s, 1H, vinyl H); 7.03 (dd, 1H, ArH J 1.7 Hz J 8.1 Hz); 7.18 (dd, 1H, ArH J 1.2 Hz J 8.2 Hz); 7.27 (d, 1H, ArH J 8.2 Hz); 7.30 (s, 1H, ArH); 7.38 (d, 1H, ArH J 8.1 Hz); 7.49 (s, 1H, ArH).

MS EI 70 eV (m/z, % intensity): 341 (M$^+$, 96%); 326 (100); 165 (64); 143 (26); 142 (35); 127 (36).

f) (Z) 1-[2-(5,6,7,87-tetrahydro-5,5,8,8-tetramethyl)naphthalenylmethylene]-2,3-dihydro-1H-indene-5-carboxylic acid (CB27871).

Potassium hydroxide (0.48 g, 8.57 mmol) is added to a suspension of (Z) 1-[2-(5,6,7,8-tetrahydro-5,5,8,8-tetramethyl(naphthalenylmethylene]-2,3-dihydro-5-cyano-1H-indene (0.13 g, 0.38 mmol) in a hydroethanolic solution (H$_2$O 0.50 ml and EtOH 4.5 ml. The mixture is refluxed with magnetic stirring for 20 hours. After cooling the reaction mixture, it is acidified with 1N HCl (15 ml), extracted with ether (3×30 ml), dried by MgSO$_4$, filtered and evaporated. The raw product is. purified by preparative HPLC on a Waters column HR C$_{18}$, (25×100 mm) with MeOH:H$_2$O=90:10+0.1% TFA as eluent. After evaporation and drying 0.07 g of a white powder is obtained (Z) 1-[2-(5,6,7,8-tetrahydro-5,5,8,8-tetramethyl)-naphthalenylmethylene]-2,3-dihydro-1H-indene-5-carboxylic acid, (CB27871) (yield=52.5%) of formula:

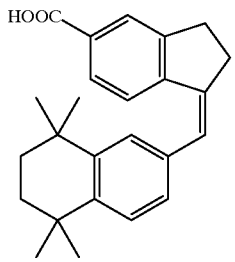

M. Pt. (° C.)=232.

NMR$^1$H 200 MHz (CDCl$_3$): 1.23 and 1.30 (2s, 12H, 5,5,8,8-Me); 1.69 (s, 4H, 6,7-CH$_2$); 2.97 (m, 4H, —CH$_2$—indene); 6.69 (s, 1H, vinyl H); 7.07 (dd, 1H, ArH J 1.3 Hz J 8.1 Hz); 7.28 (d, 1H, ArH J 8.1 Hz); 7.34 (d, 1H, ArH J 1.3 Hz); 7.41 (d, 1H, ArH J=8.3 Hz); 7.67 (dd, 1H, ArH, J 1.3 Hz J 8.3 Hz); 7.95 (s, 1H, ArH).

MS EI 70 eV (m/z, % intensity): 360 (M$^+$, 79%); 345 (M$^+$—CH$_3$, 100); 129 (46).

MSHR EI 70 eV: M$_{tr}$=360.2085 for C$_{25}$H$_{28}$O$_2$ M$_{th}$=360.2090.

HPLC: Column Waters HR C$_{18}$, 8×100 mm, 6 μ, detector UV Waters 486 to 260 nm, flow rate 3 ml/min, eluent MeOH:H$_2$O=90:10+0.1% TFA, acid (CB27871) tr=5.63 min. 99.6%.

g) (Z) 5-[1-[2-(5,6,7,8-tetrahydro-5,5,8,8-tetramethyl) naphthalenylmethylene]-2,3,-dihydro-1H-indenyl]-1H-tetrazole (CB94083).

Dibutyl tin oxide (10 mg) and trimethylsilyl azide (0.12 ml, 0.84 mmol) are added successively to a solution of (Z) 1-[2-(5,6,7,8-tetrahydro-5,5,8,8-tetramethyl-(naphthalenylmethylene]-2,3-dihydro-5-cyano-1H-indene (0.14 g, 0.42 mmol) in anhydrous toluene (0.9 ml). The reaction medium is heated for 16 hours at reflux (110° C.) under an atmosphere of argon and with magnetic stirring. After cooling, the toluene is evaporated, the product taken up in dichloromethane and incorporated onto silica. It is purified by flash chromatography on silica (eluent $CH_2Cl_2$ then $MeOH:CH_2Cl_2=5:95$). After evaporation, and then drying at the pump, 0.08 g of a white solid is obtained (Z) 5-[1-[2-(5,6,7,8-tetrahydro-5,5,8,8-tetramethyl) naphthalenylmethylene]-2,3-dihydro-1H-indenyl]-1H-tetrazole (CB94083) (yield=49.5%) of formula:

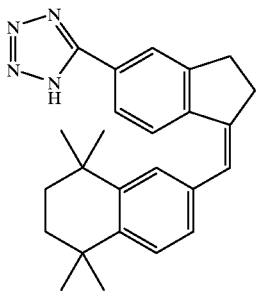

M.Pt. (° C.)=237–239.

NMR$^1$H 200 MHz (DMSO D$_6$): 1.23 and 1.25 (2s, 12H, 5,5,8,8-Me); 1.67 (s, 4H, 6,7-CH$_2$); 3.48 (s, 4H, —CH$_2$— indene); 6.40 (s, 1H, vinyl H); 7.05 (dd, 1H, ArH J 8.1 Hz J 1.7 Hz); 7.24 (d, 1H, ArH J 8.1 Hz); 7.35 (d, 1H, ArH J 1.7 Hz); 7.54 (d, 1H, ArH J 8.3 Hz); 8.01 (d, 1H, ArH J 8.3 Hz); 8.19 (s, 1H, ArH).

MS EI, 70 eV (m/z, % intensity): 384 (M$^+$, 35%); 369 (18); 356 (100), 201 (92); 143 (42); 128 (47).

MSHR EI 70 eV: $M_{tr}$=384.2309 for $C_{25}H_{28}N_4$ $M_{th}$=384.2314.

HPLC Column Waters HR C$_{18}$, 8×100 mm, 6 µ, detector UV Waters 486 to 260 nm, flow rate 3 ml/min, eluent MeOH:H$_2$O=91:9+0.1% TFA, tetrazole (CB94083) tr=2.77 min. 99.2%.

EXAMPLE 7

Preparation of (E) and (Z) 1-[2-(5,6,7,8-tetrahydro-3,5,5,8,8-pentamethyl)naphthalenylmethylene]-2,3-dihydro-1H-indene-5-carboxylic acids (CB40341 and CB75403) and (E) and (Z) 5-[1-[2-(5,6,7,8-tetrahydro-3,5,5,8,8-pentamethyl) naphthalenylmethylene]-2,3-dihydro-1H-indenyl]-1H-tetrazoles (CB23804 and CB02981).

a) (E) and (Z) 1-[2-(5,6,7,8-tetrahydro-3,5,5,8,8-pentamethyl)naphthalenylmethylene]-2,3-dihydro-5-bromo-1H-indenes.

At −70° C. a 1M solution of t-BuOK in THF (12.56 ml, 12.56 mmol) is added to a solution of (5,6,7,8-tetrahydro-3,5,5,8,8-pentamethyl-2-naphthalenyl)-6-methyl-triphenyl-phosphonium bromide (7.00 g, 12.56 mmol) in 28 ml of anhydrous THF under an argon atmosphere and with magnetic agitation. Agitation is continued at −70° C. for 1 hour before adding a solution of 5-bromo-1-indanone (1.33 g, 6.28 mmol) in 10 ml of anhydrous THF. The reaction medium is brought to ambient temperature and is stirred for 17 hours. The reaction mixture is then poured into 150 ml of an ice-water mixture and then extracted with ether (3×150 ml), dried over MgSO$_4$, filtered and evaporated. The raw product is purified by flash chromatography on silica (eluent:pure petroleum ether). 0.57 g of a white solid is obtained (Z) 1-[2-(5,6,7,8-tetrahydro-3,5,5,8,8-pentamethyl)naphthalenylmethylene]- 2,3-dihydro-5-bromo-1H-indene (yield=25%) and then 1.09 g of a white solid (E) 1-[2-(5,6,7,8-tetrahydro-3,5,5,8,8-pentamethyl) naphthalenylmethylene]-2,3-dihydro-5-bromo-1H-indene (yield=42.5%).

Isomer (Z):

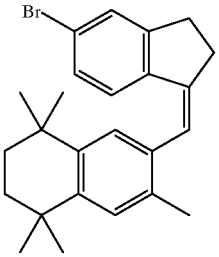

M.Pt. (° C.)=112.

NMR$^1$H 200 MHz (CDCl$_3$): 1.20 and 1.31 (2s, 12H, 5,5,8,8-Me); 1.68 (s, 4H, 6,7-CH$_2$); 2.21 (s, 3H, vinyl Me); 2.96 (m, 4H, —CH$_2$— indene); 6.53 (s, 1H, vinyl H); 6.89 (d, 1H, ArH J 8.3 Hz); 7.00 (dd, 1H, ArH J 1.7 Hz J 8.3 Hz); 7.14 (s, 1H, ArH); 7.26 (s, 1H, ArH); 7.36 (d, 1H, ArH J 1.7 Hz).

Isomer (E):

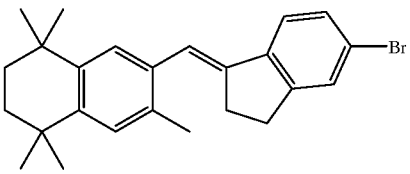

NMR$^1$H 200 MHz (CDCl$_3$): 1.29 and 1.30 (2s, 12H, 5,5,8,8-Me); 1.69 (s, 4H, 6,7-CH$_2$); 2.31 (s, 3H, Me); 3.02 (s, 4H, —CH$_2$— indene); 6.98 (s, 1H, vinyl H); 7.12 (s, 1H, ArH); 7.34 (dd, 1H, ArH J 1.5 Hz J 8.2 Hz); 7.38 (s, 1H, ArH); 7.41 (d, 1H, ArH J 1.5 Hz); 7.45 (d, 1H, ArH J 8.2 Hz).

b) (Z) 1-[2-(5,6,7,8-tetrahydro-3,5,5,8,8-pentamethyl) naphthalenylmethylene]-2,3-dihydro-5-cyano-1H-indene.

At ambient temperature, copper cyanide (0.19 g, 2.09 mmol) is added to a solution of (Z) 1-[2-(5,6,7,8-tetrahydro-3,5,5,8,8-pentamethyl(naphthalenyl-methylene]-2,3-dihydro-5-bromo-1H-indene (0.61 g, 1.49 mmol) in 10 ml of anhydrous DMF. The reaction medium is brought to reflux for 16 hours under an atmosphere of argon. After returning to ambient temperature, the reaction mixture is diluted with ether (50 ml) and filtered on celite. The organic phase is washed with a saturated aqueous solution of NaHCO$_3$ (3×50 ml) and then dried over MgSO$_4$, filtered and evaporated. The raw product is purified by flash chromatography on silica (eluent petroleum ether:ether=98:2). 0.34 g of a white solid (Z) 1-[2-(5,6,7,8-tetrahydro-3,5,5,8,8-pentamethyl (naphthalenylmethylene]-2,3-dihydro-5-cyano-1H-indene is obtained (yield=64%)

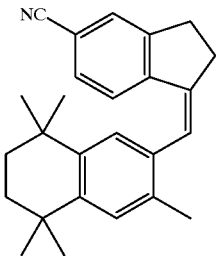

NMR¹H 200 MHz (CDCl₃): 1.17 and 1.29 (2s, 12H, 5,5,8,8-Me); 1.67 (s, 4H, 6,7-CH₂); 2.19 (s, 3H, Me); 2.98 (m, 4H, —CH₂— indene); 6.68 (s, 1H, vinyl H); 7.02–7.21 (m, 4H, ArH); 7.48 (s, 1H, ArH).

MS EI 70 eV (m/z, % intensity): 355 (M⁺, 59); 340 (M⁺—CH₃, 100); 149 (19); 142 (20); 84 (28); 73 (17); 71 (19); 57 (62); 55 (38).

c) (Z) 1-[2-(5,6,7,8-tetrahydro-3,5,5,8,8-pentamethyl)-naphthalenylmethylene]-2,3-dihydro-1H-indene-5-carboxylic acid, (CB75403).

Potassium hydroxide (0,22 g, 3.94 mmol) is added to a suspension of (Z) 1-[2-(5,6,7,8-tetrahydro-3,5,5,8,8-pentamethyl(naphthalenylmethylene]-2,3-dihydro-5-cyano-1H-indene (0.14 g, 0.39-mmol) in a hydroethanolic solution (H₂O 0.55 ml and EtOH 3.3 ml. The mixture is refluxed with magnetic stirring for 24 hours. After cooling the reaction mixture is acidified with 3N HCl, extracted with ether (3×50 ml), dried by MgSO₄, filtered and evaporated. The raw product is purified by preparative HPLC on a Waters column HR C₁₈ (25×100 mm) with MeOH:H₂O=90:10+0.1% TFA as eluent. After evaporation and drying, one obtains 0.10 g of a white solid (Z) 1-[2-(5,6,7,8-tetrahydro-3,5,5,8,8-pentamethyl)-naphthalenylmethylene]-2,3-dihydro-1H-indene-5-carboxylic acid, (CB75403) (yield=70.5%) of formula:

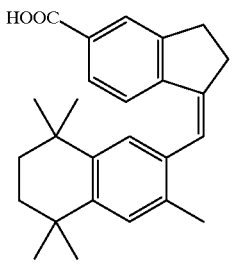

M.Pt. (° C.)=242.

NMR¹H 200 MHz (CDCl₃): 1.18 and 1.30 (2s, 12H, 5,5,8,8-Me); 1.67 (s, 4H, 6,7-CH₂); 2.20 (s, 3H, Me); 3.01 (m, 4H, —CH₂— indene); 6.66 (s broad, 1H, vinyl H); 7.10 (d, 1H, ArH J 8.2 Hz); 7.15 (s, 1H, ArH); 7.26 (s, 1H, ArH); 7.62 (dd, 1H, ArH J 1.5 Hz J 8.2 Hz); 7.95 (d, 1H, ArH J 1.5 Hz).

MS EI 70 eV (m/z, % intensity):

MSHR EI 70 eV: $M_{tr}$=360.2234 for $C_{26}H_{30}O_2$ $M_{th}$= 374.2246.

HPLC: Column Waters HR C₁₈, 8×100 mm, 6 μ, detector UV Waters 486 to 260 nm, flow rate 3 ml/min, eluent MeOH:H₂O=90:10+0.1% TFA, acid (CB75403) tr=6.36 min. 98.0%.

d) (Z) 5-[1-[2-(5,6,7,8-tetrahydro-3,5,5,8,8-pentamethyl)naphthalenylmethylene]-2,3,-dihydro-1H-indenyl]-1H-tetrazole (CB02981).

Dibutyl tin oxide (15 mg., 0.06 mmol) and trimethyl-silyl azide (0.13 ml, 1.01 mmol) are added successively to a solution of (Z) 1-[2-(5,6,7,8-tetrahydro-3,5,5,8,8-pentamethyl-(naphthalenylmethylene]-2,3-dihydro-5-cyano-1H-indene (0.18 g, 0.51 mmol) in anhydrous toluene (1.1 ml). The reaction medium is heated for 15 hours at reflux (110° C.) under an atmosphere of argon and with magnetic stirring. After cooling, the toluene is evaporated and the raw product is purified by preparative HPLC on a Waters column HR C₁₈ (25×100 mm) with MeOH:H₂O= 88:12+0.1% TFA as eluent. After evaporation and drying at the pump, one obtains 0.08 g of a white solid (Z) 5-[1-[2-(5,6,7,8-tetrahydro-3,5,5,8,8-pentamethyl)-naphthalenylmethylene]-2,3,-dihydro-1H-indenyl]-1H-tetrazole (CB02981) (yield=40%) of formula:

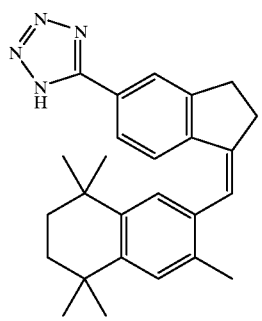

M. Pt. (° C.)=235.

NMR¹H 200 MHz (CDCl₃): 1.16 and 1.29 (2s, 12H, 5,5,8,8-Me); 1.65 (s, 4H, 6,7-CH₂); 2.21 (s, 3H, Me); 3.00 (m, 4H, —CH₂— indene); 6.64 (s broad, 1H vinyl H); 7.14 (s, 1H, ArH); 7.18 (d, 1H, ArH J 8.2 Hz); 7.27 (s, 1H, ArH); 7.54 (d, 1H, ArH J 8.1 Hz); 7.93 (s, 1H, ArH).

MS EI 70 eV (m/z, % intensity): 398 (M⁺, 72%); 371 (67), 370 (100), 355 (53); 205 (33); 157 (30); 83 (16); 69 (53); 660 (40); 57 (53); 55 (41).

MSHR EI 70 eV: $M_{tr}$=398.2474 for $C_{26}H_{30}N_4$ $M_{th}$= 398.2470.

HPLC: Column Waters HR C₁₈, 8×100 mm, 6 μ, detector UV Waters 486 to 260 nm, flow rate 3 ml/min, eluent MeOH:H₂O=90:10+0.1% TFA, tetrazole (CB02981) tr=4.4 min. 99.6%.

e) (E) 1-[2-(5,6,7,8-tetrahydro-3,5,5,8,8-pentamethyl-(naphthalenylmethylene]-2,3-dihydro-5-cyano-1H-indene.

At ambient temperature, copper cyanide (0.33 g, 3.66 mmol) is added to a solution of (E) 1-[2-(5,6,7,8-tetrahydro-3,5,5,8,8-pentamethyl(naphthalenyl-methylene]-2,3-dihydro-5-bromo-1H-indene (1.00 g, 2.44 mmol) in 10 ml of anhydrous DMF. The reaction medium is brought to reflux for 16 hours under an atmosphere of argon. After returning to ambient temperature, the reaction mixture is diluted with ether (50 ml) and filtered on celite. The organic phase is washed with a saturated aqueous solution of NaHCO₃ (3×70 ml) and then dried over MgSO₄, filtered and evaporated. The raw product is purified by flash chromatography on silica (petroleum ether:eluent ether=98:2). 0.54 g of a yellowish solid (E) 1-[2-(5,6,7,8-tetrahydro-3,5,5,8,8-pentamethyl (naphthalenylmethylene]-2,3-dihydro-5-cyano-1H-indene is obtained (yield=62%) of formula:

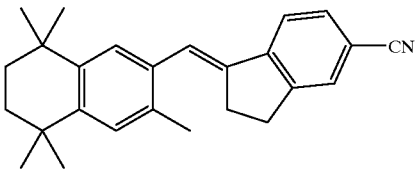

M.Pt. (° C.)=158.

NMR¹H 200 MHz (CDCl₃): 1.28 and 1.29 (2s, 12H, 5,5,8,8-Me); 1.68 (s, 4H, 6,7-CH₂); 2.32 (s, 3H, Me); 3.05 (s, 4H, —CH₂— indene); 7.11 (s, 1H, ArH); 7.12 (s, 1H, vinyl H); 7.37 (s, 1H, ArH); 7.48 (dd, 1H, ArH J 1.3 Hz J 8.0 Hz); 7.53 (s, 1H, ArH); 7.63 (d, 1H, ArH J 8.0 Hz).

MS EI 70 eV (m/z, % intensity): 355 (M⁺, 87); 340 (M⁺—CH₃, 100); 157 (14); 154 (27); 142 (47).

f) (E) 1-[2-(5,6,7,8-tetrahydro-3,5,5,8,8-pentamethyl) naphthalenylmethylene]-2,3-dihydro-1H-indene-5-carboxylic acid (CB40341).

Potassium hydroxide (0,39 g, 7.00 mmol) is added to a suspension of (E) 1-[2-(5,6,7,8-tetrahydro-3,5,5,8,8-pentamethyl(naphthalenylmethylene]-2,3-dihydro-5-cyano-1H-indene (0.25 g, 0.70 mmol) in a hydroethanolic solution (H₂O 0.55 ml and EtOH 3.3 ml. The mixture is refluxed with magnetic stirring for 16 hours. After cooling the reaction mixture, it is acidified with 3N HCl, extracted with ether (3×50 ml), dried by MgSO₄, filtered and evaporated. A solid is obtained that is washed in a mixture of pentane:ether= 90:10. After filtration and drying 0.17 g of a brown solid is obtained (E) 1-[2-(5,6,7,8-tetrahydro-3,5,5,8,8-pentamethyl)-naphthalenylmethylene]-2,3-dihydro-1H-indene-5-carboxylic acid, (CB40341) (yield=65%) of formula:

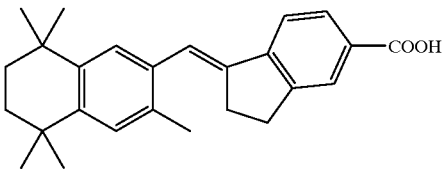

M. Pt. (° C.)=206.

NMR¹H 200 MHz (CDCl₃): 1.28 and 1.30 (2s, 12H, 5,5,8,8-Me); 1.69 (s, 4H, 6,7-CH₂); 2.34 (s, 3H, Me); 3.07 (s, 4H, —CH₂— indene); 7.13 (s, 1H, ArH),; 7.14 (s, 1H, vinyl H); 7.41 (s, 1H, ArH); 7.65 (d, 1H, ArH J 8.1 Hz); 7.93–8.10 (m, 3H, ArH).

MS EI 70 eV (m/z, % intensity): 374 (M⁺, 90%); 359 (M⁺—CH₃, 100); 129 (140).

MSHR EI 70 eV: $M_{tr}$=374.2237 for $C_{26}H_{30}O_2$ $M_{th}$=374.2246.

HPLC: Column Waters HR C₁₈, 8×100 mm, 6 μ, detector UV Waters 486 to 260 nm, flow rate 3 ml/min, eluent MeOH:H₂O=90:10+0.1% TFA, acid (CB40341) tr=7.22 min. 96.0%; impurity tr=1.22 4.0%.

g) (E) 5-[1-[2-(5,6,7,8-tetrahydro-3,5,5,8,8-pentamethyl) naphthalenylmethylene]-2,3,-dihydro-1H-indenyl]-1H-tetrazole (CB23804).

Dibutyl tin oxide (19 mg) and trimethylsilyl azide (0.20 ml, 1.52 mmol) are added successively to a solution of (E) 1-[2-(5,6,7,8-tetrahydro-3,5,5,8,8-pentamethyl-(naphthalenylmethylene]-2,3,-dihydro-5-cyano-1H-indene (0.27 g, 0.76 mmol) in anhydrous toluene (1.5 ml). The reaction medium is heated for 16 hours at reflux (110° C.) under an atmosphere of argon and with magnetic stirring. After cooling, the toluene is evaporated, and the raw product is purified by flash chromatography on silica (eluent CH₂Cl₂ then MeOH:CH₂Cl₂=5:95). After evaporation, the product is washed in a minimum of ether, filtered and then dried at the pump. 0.14 g of a white solid is obtained (E) 5-[1-[2-(5,6, 7,8-tetrahydro-3,5,5,8,8-pentamethyl) naphthalenylmethylene]-2,3-dihydro-1H-indenyl]-1H-tetrazole (CB23804) (yield=46%) of formula:

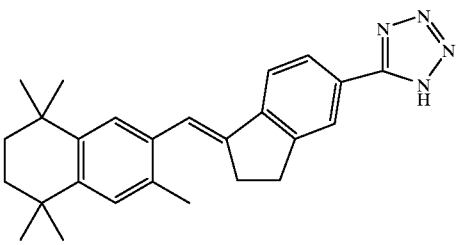

M.Pt. (° C.)=269.

NMR¹H 200 MHz (CDCl₃): 1.20 and 1.22 (2s, 12H, 5,5,8,8-Me); 1.61 (s, 4H, 6,7-CH₂); 2.26 (s, 3H, Me); 3.03 (s, 4H, —CH₂— indene); 7.03 (s, 2H, ArH and vinyl H); 7.32 (s, 1H, ArH); 7.67 (d, 1H, ArH J 8.2 Hz); 7.87 (d, 1H, ArH J 8.2 Hz); 7.92 (s, 1H, ArH).

MS EI, 70 eV (m/z, % intensity): 398 (M⁺, 72%); 370 (100); 355 (73), 340 (30); 294 (41); 215 (33); 195 (82).

MSHR EI 70 eV: $M_{tr}$=398.2476 for $C_{26}H_{30}N_4$ $M_{th}$=398.2470.

HPLC Column Waters HR C₁₈, 8×100 mm, 6 μ, detector UV Waters 486 to 260 nm, flow rate 3 ml/min, eluent MeOH:H₂O=90:10+0.1% TFA, tetrazole (CB23804) tr=4.93 min. 97.9%; impurity tr=4.13 1.3%.

EXAMPLE 8

Preparation of (E) 1-[2-(5,6,7,8-tetrahydro-3,5,5,8, 8-pentamethyl)naphthalenylmethylene]-2,3-dihydro-1H-indenyl-5-phosphonic acid (CB69179)

A suspension of (E) 1-[2-(5,6,7,8-tetrahydro-3,5,5,8,8-pentamethyl)naphthalenylmethylene]-2,3-dihydro-5-bromo-1H-indene (0.69 g, 1.68 mmol), diethyl phosphite (0.46 g, 3.37 mmol), triethylamine (0.17 g, 3.37 mmol), tetrakis(triphenylphosphine) palladium (0.20 g, 0.17 mmol) in 3 ml of anhydrous THF is refluxed for 24 hours under an atmosphere of argon and with magnetic stirring. After cooling the reaction mixture, it is taken up in ethyl acetate (100 ml) and washed with a 1N solution of HCl and then by a saturated solution of NaCl. After evaporation of the solvent, the raw product is purified by flash chromatography on silica (eluent ether:petroleum ether=10:90 then 30:70). After evaporation, one obtains 0.17 g of a white solid (E) diethyl 1-[2-(5,6,7,8-tetrahydro-3,5,5,8,8-pentamethyl)-naphthalenylmethylene]-2,3-dihydro-5-bromo-1H-indenyl-5-phosphonate (yield=22%). Using a syringe, bromotrimethylsilane (0.31 ml, 2.31 mmol) is added onto a suspension of the diethyl phosphonate (0.17 g, 0.36 mmol) in 2.3 ml of acetonitrile. The reaction mixture is refluxed for 1.5 hours under an argon atmosphere and with magnetic stirring. After cooling, it is evaporated to dryness and the raw product is purified by preparative HPLC on a Waters column HR C₁₈ (25×100 mm) with MeOH:H₂O=85:15+

0.1% TFA as eluent. After evaporation of the solvents and drying, 0.08 g of a white solid is obtained (E) 1-[2-(5,6,7,8-tetrahydro-3,5,5,8,8-pentamethyl) naphthalenylmethylene]-2,3-dihydro-1H-indenyl-5-phosphonic acid (CB69179) (yield from the diethyl phosphonate=54%) of formula:

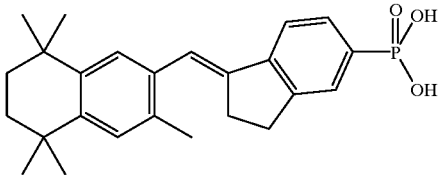

M.Pt. (° C.)=218–219 (dec.).

NMR$^1$H 200 MHz (CDCl$_3$): 1.14 and 1.23 (2s, 12H, 5,5,8,8-Me); 1.63 (s, 4H, 6,7-CH$_2$); 2.18 (s, 3H, Me); 3.35 (s, 2H, —CH$_2$— indene); 3.79 (s, 2H, —CH$_2$— indene); 6.06 (s, 1H, vinyl H); 7.05 (s, 2H, ArH); 7.41 (dd, 1H, ArH J 3.3 Hz J 7.8 Hz); 7.68 (dd, 1H, ArH J 3.3 Hz J 13.2 Hz); 7.84 (d, 1H, ArH J 13.2 Hz).

MS FAB MMA (m/z, % intensity): 411 (M$^+$+1, 100%); 395 (37); 215 (40), 154 (84); 137 (55); 136 (62).

HPLC Column Waters HR C$_{18}$, 8×100 mm, 6 $\mu$, detector UV Waters 486 to 280 nm, flow rate 3 ml/min, eluent MeOH:H$_2$O=85:15+0.1% TFA, acid (CB69179) tr=3.72 min. 99.5%.

What is claimed is:

1. An aromatic tetracyclic compound of the retinoid type having the formula:

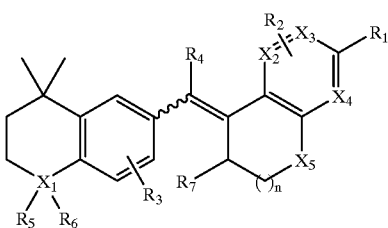

in which:

R$_1$ is selected from the group consisting of a hydrogen atom, a lower alkyl group, —PO$_3$H$_2$, —CH$_2$OH, —OH, —CHO, —COOH, —COR$_8$, —CH$_2$OCOR$_9$, —SH, —S-alkyl, —NH$_2$, —NHCOOR$_{10}$, p-hydroxyphenylaminocarbonyl, tetrazol-5-yl-aminocarbonyl, tetrazol-5-yl, 5-trifluoromethyl-tetrazoyl, and their salts with physiologically tolerated acids, where R$_{10}$ is a lower alkyl or aralkyl group and R$_8$ and R$_9$ are selected from the group consisting of a hydrogen atom, an —OH group, a lower alkyl group, —OR$_{11}$, where R$_{11}$ represents an alkyl group, which is branched or unbranched, having from 1 to 20 carbon atoms, an alkenyl group which is branched or unbranched, having from 2 to 20 carbon atoms, an aryl or aralkyl group and an amine group of formula:

in which r and r' are identical or different and represent a hydrogen atom, a lower alkyl group, an aryl or aralkyl group, an α-aminoacid group, a sugar group or a heterocyclic group in which r and r' taken together form a heterocyclic ring;

R$_2$ is selected from the group consisting of a hydrogen atom, a halogen atom, a lower alkyl group, —COOH, OR$_{11}$, —SR$_{11}$, —(CF$_2$)$_n$CF$_3$ where n is a whole number between 0 and 10, or a OCOR$_{12}$ group, their salts with physiologically tolerated acids, and an amine group of formula:

in which r and r' have the same meaning as above, and R$_{12}$ represents a hydrogen atom, a lower alkyl group, a fluoroalkyl group having 1 to 6 carbon atoms and from 3 to 7 fluorine atoms, an aryl group or an aralkyl group;

R$_3$ is selected from the group consisting of a hydrogen atom, a lower alkyl group, a halogen atom, a fluoroalkyl group having from 1 to 6 carbon atoms and from 3 to 7 fluorine atoms, or —OR$_{13}$ where R$_{13}$ represents a hydrogen atom, a lower alkyl group, an aryl group, an aralkyl group, or a trifluoromethyl group;

X$_1$ is selected from the group consisting of an atom of carbon, an atom of oxygen and an atom of sulfur;

R$_5$ and R$_6$ are:
methyl or ethyl groups, when X$_1$ is an atom of carbon,
do not exist when X$_1$ is an atom of oxygen or an atom of sulfur,
one or two atoms of oxygen when X$_1$ is an atom of sulfur in the form of a sulphoxide —SO— or a sulphone —SO$_2$—

R$_4$ is selected from the group consisting of a hydrogen atom, a halogen atom, a trifluoromethyl group, an aryl group, an aralkyl group, and a lower alkyl group, unsubstituted or substituted with a hydroxyl group, one or more atoms of fluorine, a lower alkoxy group or by —(C=O)R$_{14}$ in which R$_{14}$ represents a hydrogen atom, a lower group, a hydroxyl group, a lower alkoxy group or an amine group of formula:

in which r and r' have the same meaning as above;

X$_2$ and X$_3$, identical or different, represent an atom of carbon, an atom of oxygen or an atom of nitrogen, or X$_2$–X$_3$ is a single atom of sulfur, oxygen or nitrogen, wherein the nucleus carrying X$_2$ and X$_3$ is selected from the group consisting of a benzene, pyridine, thiophene, furane, and pyrrole nucleus;

R$_7$ is selected from the group consisting of a hydrogen atom, a trifluoromethyl group, a lower alkyl group, unsubstituted or substituted with one or more atoms of fluorine, and —$OR_{15}$ where $R_{15}$ represents a hydrogen atom or a lower alkyl group;

$X_4$ represents a carbon atom or a nitrogen atom;

$X_5$ is selected from the group consisting of a carbon, oxygen, sulfur, nitrogen atom, —S—, —SO—, —$SO_2$—, —$NR_{16}$— where $R_{16}$ represents a hydrogen atom or a lower alkyl group, and —$COR_{17}$— or —$CO_2R_{17}$— where $R_{17}$ is a lower alkyl group or a benzyl group; and n is 0 or 1.

2. A compound according to claim 1, wherein $R_2$ represents a hydrogen atom and $R_1$ is selected from the group consisting of a —COOH group, a —$PO_3H_2$ group and a —$CONH_2$ group.

3. A compound selected from the group consisting of (E) 3-[2-(5,6,7,8-tetrahydro-5,5,8,8-tetramethyl)-naphthalenylmethylene]-dihydro-benzo furane-5-carboxylic acid, (Z) 1-[2-(5,6,7,8-tetrahydro-5,5,8,8-tetramethyl)-naphthalenylmethylene]-1,2,3,4-tetrahydronaphthalene-6-carboxylic acid, (E) 1-[2-(5,6,7,8-tetrahydro-5,5,8,8-tetramethyl)-naphthalenylmethylene]-1,2,3,4-tetrahydronaphthalene-6-carboxylic acid, (E) 5-[1-[2-(5,6,7,8-tetrahydro-5,5,8,8-tetramethyl)-2-naphthalenylmethylene]-1,2,3,4-tetrahydronaphthalenyl]-1H-tetrazole, (Z) 1-[2-(5,6,7,8-tetrahydro-3,5,5,8,8-pentamethyl)-naphthalenylmethylene]-1,2,3,4-tetrahydronaphthalene-6-carboxylic acid, (E) 1-[2-(5,6,7,8-tetrahydro-3,5,5,8,8-pentamethyl)-naphthalenylmethylene]-1,2,3,4-tetrahydronaphthalene-6-carboxylic acid, (Z) 5-[1-[2-(5,6,7,8-tetrahydro-3,5,5,8,8-pentamethyl)-2-naphthalenylmethylene]-1,2,3,4-tetrahydronaphthalenyl]-1H-tetrazole, (E) 5-[1-[2-(5,6,7,8-tetrahydro-3,5,5,8,8-pentamethyl)-2-naphthalenylmethylene]-1,2,3,4-tetrahydronaphthalenyl]-1H-tetrazole, (E) 1-[2-(5,6,7,8-tetrahydro-5,5,8,8-tetramethyl)-naphthalenylmethylene]-2,3-dihydro-1H-indene-5-carboxylic acid, (E) 5-[1-[2-(5,6,7,8-tetrahydro-5,5,8,8-tetramethyl)-naphthalenylmethylene]-2,3,-dihydro-1H-indenyl]-1H-tetrazole, (Z) 1-[2-(5,6,7,8-tetrahydro-5,5,8,8-tetramethyl)-naphthalenylmethylene]-2,3-dihydro-1H-indene-5-carboxylic acid, (Z) 5-[1-[2-(5,6,7,8-tetrahydro-5,5,8,8-tetramethyl)-naphthalenylmethylene]-2,3,-dihydro-1H-indenyl]-1H-tetrazole, (Z) 1-[2-(5,6,7,8-tetrahydro-3,5,5,8,8-pentamethyl)-naphthalenylmethylene]-2,3-dihydro-1H-indene-5-carboxylic acid, (Z) 5-[1-[2-(5,6,7,8-tetrahydro-3,5,5,8,8-pentamethyl)-naphthalenylmethylene]-2,3,-dihydro-1H-indenyl]-1H-tetrazole, (E) 1-[2-(5,6,7,8-tetrahydro-3,5,5,8,-pentamethyl)-naphthalenylmethylene]-2,3-dihydro-1H-indene-5-carboxylic acid, (E) 5-[1-[2-(5,6,7,8-tetrahydro-3,5,5,8,8-pentamethyl)-naphthalenylmethylene]-2,3,-dihydro-1H-indenyl]-1H-tetrazole, (E) 1-[2-(5,6,7,8-tetrahydro-3,5,5,8,8-pentamethyl)-naphthalenylmethylene]-2,3-dihydro-1H-indenyl-5-phosphonic acid, 1-[(E)-2-(5,6,7,8-tetrahydro-5,5,8,8-tetramethyl)-naphthalenylmethylene]-2,3-dihydro-2-methyl-1H-indene-5-carboxylic acid, (Z) 1-[2-(5,6,7,8-tetrahydro-5,5,8,8-tetramethyl)-naphthalenylmethylene]-2,3-dihydro-2-methyl-1H-indene-5-amide, (Z) 1-[-2-(5,6,7,8-tetrahydro-5,5,8,8-tetramethyl)-naphthalenylmethylene]-2,3-dihydro-2-methyl-1H-indene-5-carboxylic acid and (E) 5-[1-[2-(5,6,7,8-tetrahydro-5,5,8,8-tetramethyl)-naphthalenylmethylene]-2,3-dihydro-2-methyl-1H-indenyl]-1H-tetrazole.

4. A therapeutic, dermatological or cosmetic composition including at least one compound of the formula defined in claim 1 in the form of a pharmaceutically acceptable salt or ester.

5. A therapeutic, dermatological or cosmetic composition including at least one compound of the Formula defined in claim 2 in the form of a pharmaceutically acceptable salt or ester.

6. A therapeutic, dermatological or cosmetic composition including at least one compound of the formula defined in claim 3 in the form of a pharmaceutically acceptable salt or ester.

7. A therapeutic composition comprising at least one compound of the formula defined in claim 1 and a carrier.

8. A therapeutic composition comprising at least one compound of the formula defined in claim 2 and a carrier.

9. A therapeutic composition comprising at least one compound of the formula defined in claim 3 and a carrier.

10. A therapeutic composition comprising at least one compound of the formula defined in claim 1 and a diluent.

11. A therapeutic composition comprising at least one compound of the formula defined in claim 2 and a diluent.

12. A therapeutic composition comprising at least one compound of the formula defined in claim 3 and a diluent.

* * * * *